United States Patent
Luengo et al.

(10) Patent No.: US 6,670,387 B1
(45) Date of Patent: Dec. 30, 2003

(54) THROMBOPOIETIN MIMETICS

(75) Inventors: Juan I. Luengo, Audubon, PA (US); Kevin J. Duffy, Norristown, PA (US); Stephen G. Miller, San Diego, CA (US)

(73) Assignees: SmithKline Beecham Corporation, Philadelphia, PA (US); Ligand Pharmaceuticals, San Diego, CA (US)

( * ) Notice: Subject to any disclaimer, the term of this patent is extended or adjusted under 35 U.S.C. 154(b) by 0 days.

(21) Appl. No.: 09/868,198

(22) PCT Filed: Dec. 17, 1999

(86) PCT No.: PCT/US99/30371

§ 371 (c)(1), (2), (4) Date: Jun. 14, 2001

(87) PCT Pub. No.: WO00/35446

PCT Pub. Date: Jun. 22, 2000

Related U.S. Application Data

(60) Provisional application No. 60/153,364, filed on Sep. 10, 1999, and provisional application No. 60/112,614, filed on Dec. 17, 1998.

(51) Int. Cl.[7] .................. A61K 31/136; A61K 31/4402; A61K 31/415; C07D 231/20
(52) U.S. Cl. .................. 514/407; 514/341; 514/657; 548/374; 548/375; 548/376
(58) Field of Search ................... 514/341, 407, 514/657; 548/374, 375, 376

(56) References Cited

U.S. PATENT DOCUMENTS

| 4,510,149 A | 4/1985 | Cozzi et al. ................. 514/341 |
| 4,880,788 A | 11/1989 | Moake et al. ................ 514/150 |

FOREIGN PATENT DOCUMENTS

| EP | 1 207 155 | 7/2000 |
| EP | 1 104 674 | 6/2001 |
| GB | 779 880 | 7/1957 |
| WO | WO 98/46606 | 10/1998 |

OTHER PUBLICATIONS

A. Esteve, Ann. Pharm. Franc., 1950, vol. 8, No. 9–10, pp. 594–604.
Morris, et al., Anti–Cancer Drugs, 1997, vol. 8, No. 8, pp. 746–755.
Duffy, et al., J. Med. Chem., 2001, vol. 44, No. 22, pp. 3730–3745.
Yamazaki, et al., Database HCAPLUS, AN 1995: Abstract, 196968.
Bartley, et al., Cell, 1994, vol. 77, pp. 1117–1124.

*Primary Examiner*—Phyllis G. Spivack
(74) *Attorney, Agent, or Firm*—Wayne J. Dustman; Stephen Venetianer; Charles M. Kinzig

(57) ABSTRACT

Non-peptide TPO mimetics are disclosed, as well as a method of treating thrombocytopenia, in a mammal, including a human, in need thereof, which comprises administering to such mammal an effective amount of a selected hydroxy-1-azo-naphthalene derivative.

15 Claims, No Drawings

THROMBOPOIETIN MIMETICS

This is a 371 of International Application PCT/US99/30371, Filed Dec. 17, 1999, which claims benefit from the following Provisional Application: No. 60/153,364, filed Sep. 10, 1999 and No. 60/112,614, filed Dec. 17, 1998.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538 (1994). Thrombopoietin is a glycoprotein with two distinct regions separated by a potential Arg—Arg cleavage site. The amino-terminal region is highly conserved in man and mouse, and has some homology with erythropoietin and interferon-alpha and interferon-beta. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoietin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression is restricted to spleen, bone marrow, or fetal liver in mice (see Souyri et al. *Cell* 63: 1137–1147 (1990)) and to megakaryocytes, platelets, and CD34+ cells in humans (see Methia et al. *Blood* 82: 1395–1401 (1993)). Further evidence for TPO-R as a key regulator of megakaryopoiesis is the fact that exposure of CD34+ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration.

It would be desirable to provide compounds which allow for the treatment of thrombocytopenia by acting as a TPO mimetic.

As disclosed herein it has unexpectedly been discovered that certain hydroxy-1-azo-naphthalene derivatives are effective as agonists of the TPO receptor, they are potent TPO mimetics.

SUMMARY OF THE INVENTION

This invention relates to compounds of Formula (I):

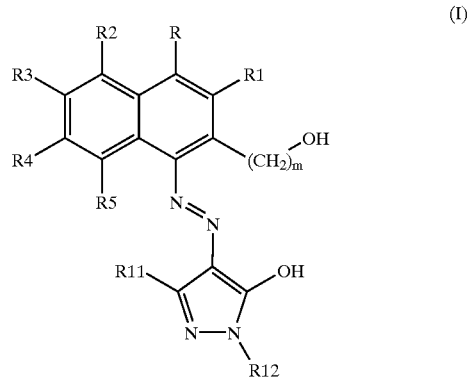

wherein:
R, $R^1$, $R^2$, $R^3$, $R^4$, $R^5$ and $R^{11}$ are each independently selected from hydrogen, —C(O)$OR^6$, —CONR$^9$$R^{10}$, phosphonic acid, phosphinic acid, $C_{1-6}$alkyl, $C_{1-6}$alkoxy, —$(CH_2)_pOR^6$, nitro, cyano, halogen, —$NR^9R^{10}$, N-acylamino, N-sulfonylamino, —$S(O)_nR^6$, $C_5$–$C_{12}$aryl, substituted $C_5$–$C_{12}$aryl, alkyl, cycloalkyl, substituted cycloalkyl, protected —OH, and alkyl substituted with one or more substituents selected from the group consisting of: alkoxy, acyloxy, $C_5$–$C_{12}$aryl, substituted $C_5$–$C_{12}$aryl, —$NR^9R^{10}$, N-acylamino, oxo, hydroxy, cycloalkyl, substituted cycloalkyl, —$C(O)OR^6$, —$C(O)NR^9R^{10}$, —$S(O)_2NR^9R^{10}$, —$S(O)_nR^6$, aryloxy, nitro, cyano, halogen, and protected —OH; where n is 0–3;

p is 0–6;

$R^6$ is selected from hydrogen, alkyl, cycloalkyl, $C_6$–$C_{12}$aryl, substituted alkyl, substituted cycloalkyl and substituted $C_6$–$C_{12}$aryl; and $R^9$ and $R^{10}$ are independently selected from hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, —$NR^6R^6$, N-acylamino, oxo, hydroxy, —$C(O)OR^6$, —$S(O)_nR^6$, —$C(O)NR^6R^6$, —$S(O)_2NR^6R^6$, nitro, cyano, cycloalkyl, substituted cycloalkyl, $C_5$–$C_{12}$aryl, substituted $C_5$–$C_{12}$aryl and protected —OH where n and $R^6$ are as described above; or $R^9$ and $R^{10}$ taken together with the nitrogen to which they are attached represent a 5 to 6 member saturated ring containing up to one other heteroatom selected from oxygen and nitrogen;

m is 0–6; and $R^{12}$ is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, cycloalkyl, substituted cycloalkyl, $C_5$–$C_{12}$aryl, substituted $C_5$–$C_{12}$aryl, aryloxy, alkoxy, acyloxy, amino, nitro, cyano, halogen, hydroxy, protected —OH, and alkyl substituted with one or more substituents selected from the group consisting of: alkoxy, acyloxy, $C_5$–$C_{12}$aryl, substituted $C_5$–$C_{12}$aryl, cycloalkyl, substituted cycloalkyl, aryloxy, amino, nitro, cyano, halogen, hydroxy, and protected —OH; and pharmaceutically acceptable salts, hydrates, solvates and esters thereof;

provided that:

at least one of R, $R^1$, $R^2$, $R^3$, $R^4$, $R^5$ or $R^{11}$ is selected from: sulfonic acid, —$C(O)OR^6$, —$CONR^9R^{10}$, phosphonic acid and phosphinic acid; where $R^6$, $R^9$ and $R^{10}$ are as described above; and provided that:

when R is sulfonic acid, $R^{12}$ does not equal unsubstituted phenyl or 4-methylphenyl.

This invention relates to a method of treating thrombocytopenia, which comprises administering to a subject in need thereof an effective amount of a TPO mimetic compound of Formula (II):

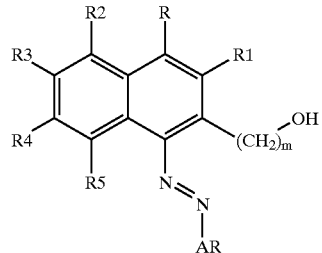

(II)

wherein:

R, $R^1$, $R^2$, $R^3$, $R^4$ and $R^5$ are each independently selected from hydrogen, —$C(O)OR^6$, —$CONR^9R^{10}$, —$SO_2NR^9R^{10}$, phosphonic acid, phosphinic acid, $C_{1-6}$alkyl, $C_{1-6}$alkoxy, —$(CH_2)_pOR^6$, nitro, cyano, halogen, —$NR^9R^{10}$, N-acylamino, N-sulfonylamino, —$S(O)_nR^6$, $C_5$–$C_{12}$aryl, substituted $C_5$–$C_{12}$aryl, alkyl, cycloalkyl, substituted cycloalkyl, protected —OH, and alkyl substituted with one or more substituents selected from the group consisting of: alkoxy, acyloxy, $C_5$–$C_{12}$aryl, substituted $C_5$–$C_{12}$aryl, —$NR^9R^{10}$, N-acylamino, oxo, hydroxy, cycloalkyl, substituted cycloalkyl, —$C(O)OR^6$, —$C(O)NR^9R^{10}$, —$S(O)_2NR^9R^{10}$, —$S(O)_nR^6$, aryloxy, nitro, cyano, halogen, and protected —OH; where n is 0 to 3;

p is 0–6;

$R^6$ is selected from hydrogen, alkyl, cycloalkyl, $C_6$–$C_{12}$aryl, substituted alkyl, substituted cycloalkyl and substituted $C_6$–$C_{12}$aryl, and $R^9$ and $R^{10}$ are independently selected from hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, —$NR^6R^6$, N-acylamino, oxo, hydroxy, —$C(O)OR^6$, —$S(O)_nR^6$, —$C(O)NR^6R^6$, —$S(O)_2NR^6R^6$, nitro, cyano, halogen, cycloalkyl, substituted cycloalkyl, $C_5$–$C_{12}$aryl, substituted $C_5$–$C_{12}$aryl and protected —OH where n and $R^6$ are as described above; or $R^9$ and $R^{10}$ taken together with the nitrogen to which they are attached represent a 5 to 6 member saturated ring containing up to one other heteroatom selected from oxygen and nitrogen;

m is 0–6; and

AR is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring at least one heteroatom, optionally substituted with one or more substituents selected from the group consisting of: alkyl, cycloalkyl, substituted cycloalkyl, $C_5$–$C_{12}$aryl, substituted $C_5$–$C_{12}$aryl, aryloxy, hydroxy, alkoxy, acyloxy, —$NR^7R^8$, N-acylamino, N-sulfonylamino, nitro, cyano, halogen, —$C(O)OR^6$, —$C(O)NR^7R^8$, —$S(O)_2NR^7R^8$, —$S(O)_nR^6$, protected —OH, and alkyl substituted with one or more substituents selected from the group consisting of: alkoxy, acyloxy, $C_5$–$C_{12}$aryl, substituted $C_5$–$C_{12}$aryl, —$NR^6R^6$, N-acylamino, oxo, hydroxy, cycloalkyl, substituted cycloalkyl, —$C(O)OR^6$, —$C(O)NR^7R^8$, —$S(O)_2NR^7R^8$, —$S(O)_nR^6$, aryloxy, nitro, cyano, halogen, and protected —OH; where n is 0 to 3;

$R^6$ is selected from hydrogen, alkyl, cycloalkyl, $C_6$–$C_{12}$aryl, substituted alkyl, substituted cycloalkyl and substituted $C_6$–$C_{12}$aryl; and $R^7$ and $R^8$ are independently hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, —$NR^6R^6$, N-acylamino, oxo, hydroxy, —$C(O)OR^6$, —$S(O)_n$$R^6$, —$C(O)NR^6R^6$, —$S(O)_2NR^6R^6$, nitro, cyano, cycloalkyl, substituted cycloalkyl, halogen, $C_6$–$C_{12}$aryl, substituted $C_6$–$C_{12}$aryl and protected —OH where n and $R^6$ are as described above; and pharmaceutically acceptable salts, hydrates, solvates and esters thereof.

The present invention also relates to the discovery that the compounds of Formula (II) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Preferred among the presently invented Formula (I) compounds are those in which R is not hydrogen.

Preferred among the presently invented Formula (I) compounds are those in which $R^1$, $R^2$, $R^3$, $R^4$ and $R^5$ are each independently selected from hydrogen, $C_{1-6}$alkyl, $C_{1-6}$alkoxy, —$(CH_2)_pOR^6$, —$C(O)OR^6$, nitro, cyano, halogen, $C_5$–$C_{12}$aryl, —$S(O)_nR^6$, cycloalkyl and protected —OH, where p is 0–6, $R^6$ is selected from hydrogen, alkyl, cycloalkyl, $C_6$–$C_{12}$aryl, substituted alkyl, substituted cycloalkyl and substituted $C_6$–$C_{12}$aryl, and n is 0–3.

Preferred among the presently invented Formula (I) compounds are those in which R is carboxylic acid or sulfonic acid; $R^1$, $R^2$, $R^3$, $R^4$ and $R^5$ are each independently selected from hydrogen, $C_{1-6}$alkoxy, nitro, $C_{1-6}$alkyl, hydroxy and halogen; m is 0; and $R^{12}$ is a cyclic or polycyclic aromatic ring containing from 3 to 14 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, $C_6$–$C_{12}$aryl, substituted cycloalkyl, substituted $C_6$–$C_{12}$aryl, aryloxy, alkoxy, trifluoromethyl, cycloalkyl, nitro, cyano, hydroxy, substituted alkyl, halogen and protected —OH; and pharmaceutically acceptable salts, hydrates, solvates and esters thereof.

Particularly preferred among the presently invented Formula (I) compounds are those in which R is carboxylic acid or sulfonic acid; $R^1$, $R^2$, $R^3$, $R^4$ and $R^5$ are each independently selected from hydrogen, $C_{1-6}$alkoxy, $C_{1-6}$alkyl and halogen; m is 0; and $R^{12}$ is phenyl substituted with one or more substituents selected from the group consisting of: alkyl, substituted alkyl, $C_6$–$C_{12}$ aryl, substituted $C_6$–$C_{12}$aryl, aryloxy, alkoxy, trifluoromethyl, halogen, hydroxy and protected —OH; and pharmaceutically acceptable salts, hydrates, solvates and esters thereof.

The most preferred among the presently invented Formula (I) compounds are those in which R is carboxylic acid or sulfonic acid; $R^1$, $R^2$, $R^3$, $R^4$ and $R^5$ are each independently selected from hydrogen, $C_{1-6}$alkoxy, $C_{1-6}$alkyl and halogen; m is 0; and $R^{12}$ is phenyl substituted with from one to three substituents selected from the group consisting of: alkyl, $C_6$–$C_{12}$ aryl, substituted $C_6$–$C_{12}$aryl, hydroxy, alkoxy, trifluoromethyl and halogen; and pharmaceutically acceptable salts, hydrates, solvates and esters thereof.

Preferred among the presently invented compounds are:

4-{[1-(4-chlorophenyl)-5-hydroxy-3-methyl-1H-pyrazol-4-yl]azo}-3-hydroxy-1-naphthalenesulfonic acid;

4-{[(3-chlorophenyl)-5-hydroxy-3-methyl-1H-pyrazol-4-yl]azo}-3-hydroxy-1-naphthalenesulfonic acid;

3-hydroxy-4-[(5-hydroxy-3-methyl-1-phenyl-1H-pyrazol-4-yl)azo]-1-naphthalenecarboxylic acid;

3-hydroxy-4-{[5-hydroxy-3-methyl-1-(4-methylphenyl)-1H-pyrazol-4-yl]azo}-1-naphthalenecarboxylic acid;

3-hydroxy-4-{[5-hydroxy-3-methyl-1-(4-nitrophenyl)-1H-pyrazolyl-4-yl]azo}-1-naphthalenesulfonic acid;

4-{[3-tert-butyl-5-hydroxy-1-methyl-1H-pyrazol-4-yl]azo}-3-hydroxy-1-naphthalenesulfonic acid;

4-{[3-tert-butyl-5-hydroxy-1-phenyl-1H-pyrazol-4-yl]azo}-3-hydroxy-1-naphthalenesulfonic acid;

3-hydroxy-4-[(5-hydroxy-3-methyl-1-pyridin-2-yl-1H-pyrazol-4-yl)azo]-1-naphthalenesulfonic acid;

4-{[1-(4-benzyloxyphenyl)-5-hydroxy-3-methyl-1H-pyrazol-4-yl]azo}-3-hydroxy-1-naphthalenesulfonic acid;

3-hydroxy-4-{[5-hydroxy-3-methyl-1-(3-trifluoromethylphenyl)-1H-pyrazol-4-yl]azo}-1-naphthalenesulfonic acid;

4-{[1-(3,4-dimethylphenyl)-5-hydroxy-3-methyl-1H-pyrazol-4-yl]azo}-3-hydroxy-1-naphthalenesulfonic acid;

3-hydroxy-4-{[5-hydroxy-3-methyl-1-(3-nitrophenyl)-1H-pyrazol-4-yl]azo}-1-naphthalenesulfonic acid;

4-{[1-(4-fluorophenyl)-5-hydroxy-3-methyl-1H-pyrazol-4-yl]azo}-3-hydroxy-1-naphthalenesulfonic acid;

3-hydroxy-4-{[5-hydroxy-1-(4-iodophenyl)-3-methyl-1H-pyrazol-4-yl]azo}-1-naphthalenesulfonic acid;

3-hydroxy-4-{[5-hydroxy-3-methyl-1-(2-nitrophenyl)-1H-pyrazol-4-yl]azo}-1-naphthalenesulfonic acid;

4-{[1-(3,4-dimethylphenyl)-3-ethoxy-5-hydroxy-1H-pyrazol-4-yl]azo}-3-hydroxy-1-naphthalenesulfonic acid;

3-hydroxy-4-{[5-hydroxy-3-methyl-1-(4-trifluoromethylphenyl)-1H-pyrazol-4-yl]azo}-1-naphthalenesulfonic acid;

3-hydroxy-4-{[5-hydroxy-3-methyl-1-(3-methylphenyl)-1H-pyrazol-4-yl]azo}-1-naphthalenesulfonic acid;

4-{[3-tert-butyl-1-(3,4-dimethylphenyl)-5-hydroxy-1H-pyrazol-4-yl]azo}-3-hydroxy-1-naphthalenesulfonic acid;

4-{[1-(3,4-dimethylphenyl)-5-hydroxy-3-phenyl-1H-pyrazol-4-yl]azo}-3-hydroxy-1-naphthalenesulfonic acid;

4-{[1-(3,4-Dimethylphenyl)-5-hydroxy-3-methyl-1H-pyrazol-4-yl]azo}-3-hydroxy-1-napthalenecarboxylic acid;

Methyl 5-{[1-(3,4-dimethylphenyl)-5-hydroxy-3-methyl-1H-pyrazo-4-yl]azo}-6-hydroxy-2-napthalenecarboxylate;

1-{[1-(3,4Dimethylphenyl)-5-hydroxy-3-methyl-1H-pyrazol-4-yl]azo}-2-hydroxynaphthalene; and 4-[(1-Benzyl-5-hydroxy-3-methyl-1H-pyrazol-4-yl)azo]-3-hydroxy-1-naphthalenesulfonic acid.

This invention also relates to Compounds of Formula (II), as described above, which are included in the pharmaceutical compositions of the invention and used in the methods of the invention.

Preferred among the presently invented Formula II compounds are those in which R is not hydrogen.

Preferred among the presently invented Formula II compounds are those in which $R^1$, $R^2$, $R^3$, $R^4$ and $R^5$ are each independently selected from hydrogen, $C_{1-6}$alkyl, $C_{1-6}$alkoxy, —$(CH_2)_pOR^6$, —$C(O)OR^6$, nitro, cyano, halogen, $C_5$–$C_{12}$aryl, $S(O)_nR^6$, cycloalkyl and protected —OH,
  where p is 0–6,
  $R^6$ is selected from hydrogen, alkyl, cycloalkyl, $C_6$–$C_{12}$aryl, substituted alkyl, substituted cycloalkyl and substituted $C_6$–$C_{12}$aryl, and
  n is 0–3.

Preferred among the presently invented Formula II compounds are those in which R is carboxylic acid or sulfonic acid; $R^1$, $R^2$, $R^3$, $R^4$ and $R^5$ are each independently selected from hydrogen, $C_{1-6}$alkoxy, nitro, $C_{1-6}$alkyl and halogen; m is 0; and AR is cyclic or polycyclic aromatic $C_3$–$C_{14}$, optionally containing from one to three heteroatoms, provided that when C is 3 the aromatic ring contains at least two heteroatoms and when C is 4 the aromatic ring contains at least one heteroatom, and optionally substituted with one or more substituents selected from the group consisting of: alkyl, $C_6$–$C_{12}$ aryl, substituted cycloalkyl, substituted $C_6$–$C_{12}$aryl, aryloxy, hydroxy, alkoxy, cycloalkyl, amino, nitro, cyano, halogen and protected —OH; and pharmaceutically acceptable salts, hydrates, solvates and esters thereof.

Also preferred among the presently invented Formula II compounds are those in which R is carboxylic acid or sulfonic acid; $R^1$, $R^2$, $R^3$, $R^4$ and $R^5$ are each independently selected from hydrogen, $C_{1-6}$alkoxy, $C_{1-6}$alkyl and halogen; m is 0; and AR is cyclic or polycyclic aromatic $C_3$–$C_{14}$, optionally containing from one to three heteroatoms, provided that when C is 3 the aromatic ring contains at least two heteroatoms and when C is 4 the aromatic ring contains at least one heteroatom, and optionally substituted with one or more substituents selected from the group consisting of: alkyl, $C_6$–$C_{12}$ aryl, substituted $C_6$–$C_{12}$aryl, aryloxy, hydroxy, alkoxy, amino, halogen and protected —OH; and pharmaceutically acceptable salts, hydrates, solvates and esters thereof.

Also preferred among the presently invented Formula II compounds are those in which R is carboxylic acid or sulfonic acid; $R^1$, $R^2$, $R^3$, $R^4$ and $R^5$ are each independently selected from hydrogen, $C_{1-6}$alkoxy, $C_{1-6}$alkyl and halogen; m is 0; and AR is selected from naphthalene, phenyl and pyrazole, and optionally substituted with from one to three substituents selected from the group consisting of: alkyl, $C_6$–$C_{12}$ aryl, substituted $C_6$–$C_{12}$aryl, hydroxy, alkoxy, hydroxy and halogen; and pharmaceutically acceptable salts, hydrates, solvates and esters thereof.

Preferred among the compounds of Formula II are those in which R is carboxylic acid or sulfonic acid; $R^1$, $R^2$, $R^3$, $R^4$ and $R^5$ are each independently selected from hydrogen, $C_{1-6}$alkoxy, nitro, $C_{1-6}$alkyl and halogen; m is 0; and AR is a cyclic or polycyclic aromatic ring containing from 3 to 14 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, $C_6$–$C_{12}$ aryl, substituted cycloalkyl, substituted $C_6$–$C_{12}$aryl, aryloxy, hydroxy, alkoxy, cycloalkyl, trifluoromethyl, amino, nitro, cyano, halogen, hydroxy and protected —OH; and pharmaceutically acceptable salts, hydrates, solvates and esters thereof.

Particularly preferred among the compounds of Formula II are those in which R is carboxylic acid or sulfonic acid; $R^1$, $R^2$, $R^3$, $R^4$ and $R^5$ are each independently selected from hydrogen, $C_{1-6}$alkoxy, $C_{1-6}$alkyl and halogen; m is 0; and AR is a cyclic or polycyclic aromatic ring containing from 3 to 14 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, $C_6$–$C_{12}$ aryl, substituted $C_6$–$C_{12}$aryl, aryloxy, hydroxy, alkoxy, amino, trifluoromethyl, halogen, hydroxy and protected —OH; and pharmaceutically acceptable salts, hydrates, solvates and esters thereof.

The most preferred among the compounds of Formula II are those in which R is carboxylic acid or sulfonic acid; $R^1$, $R^2$, $R^3$, $R^4$ and $R^5$ are each independently selected from hydrogen, $C_{1-6}$alkoxy, $C_{1-6}$alkyl and halogen; m is 0; and AR is selected from naphthalene, phenyl and pyrazole, and optionally substituted with from one to three substituents selected from the group consisting of: alkyl, $C_6$–$C_{12}$ aryl, substituted $C_6$–$C_{12}$aryl, hydroxy, alkoxy, trifluoromethyl and halogen; and pharmaceutically acceptable salts, hydrates, solvates and esters thereof.

Preferred among the compounds of Formula II are:

3-hydroxy-4-[(2-hydroxy-1-naphthalenyl)azo]-7-nitro-1-naphthalenesulfonic acid;
3-hydroxy-4-[(1-hydroxy-2-naphthalenyl)azo]-7-nitro-1-naphthalenesulfonic acid;
3-hydroxy-4-[(2-hydroxy-1-naphthalenyl)azo]-1-naphthalenesulfonic acid;
3-hydroxy-4-[(2-hydroxy-5-methyl-1-phenyl)azo]-1-naphthalenesulfonic acid;
3-hydroxy-4-[(1-hydroxy-2-naphthalenyl)azo]-1-naphthalenesulfonic acid;
3-hydroxy-4-[(5-hydroxy-3-methyl-1-phenyl-1H-pyrazol-4-yl)azo]-1-naphthalenesulfonic acid;
3-hydroxy-4-[(10-hydroxy-9-phenanthrenyl)azo]-1-naphthalenesulfonic acid;
3-hydroxy-4-[(2-hydroxy-7-methoxy-1-naphthalenyl)azo]-1-naphthalenesulfonic acid;
3-hydroxy-4-[(4-hydroxy-2-methoxy-1-naphthalenyl)azo]-1-naphthalenesulfonic acid;
4-[(1,3-dimethyl-5-hydroxy-1H-pyrazol-4-yl)azo]-3-hydroxy-1-naphthalenesulfonic acid;
3-hydroxy-4-{[5-hydroxy-1-(4-methylphenyl)-3-methyl-1H-pyrazol-4-yl]azo}-1-naphthalenesulfonic acid;
4-{[1-(4-chlorophenyl)-5-hydroxy-3-methyl-1H-pyrazol-4-yl]azo}-3-hydroxy-1-naphthalenesulfonic acid;
4-{[(3-chlorophenyl)-5-hydroxy-3-methyl-1H-pyrazol-4-yl]azo}-3-hydroxy-1-naphthalenesulfonic acid;
3-hydroxy-4-[(5-hydroxy-3-methyl-1-phenyl-1H-pyrazol-4-yl)azo]-1-naphthalenecarboxylic acid;
3-hydroxy-4-{[5-hydroxy-3-methyl-1-(4-methylphenyl)-1H-pyrazol-4-yl]azo}-1-naphthalenecarboxylic acid;
4-{1-[3-(N-ethylsulfonamidophenyl)-5-hydroxy-3-methyl-1H-pyrazol-4-yl]azo}-3-hydroxy-1-naphthalenesulfonic acid;

4-[(3-ethoxycarbonyl-5-hydroxy-1-phenyl-1H-pyrazol-4-yl)azo]-3-hydroxy-1-naphthalenesulfonic acid;
3-hydroxy-4-{[5-hydroxy-3-methyl-1-(4-nitrophenyl)-1H-pyrazol-4-yl]azo}-1-naphthalenesulfonic acid;
4-{[3-tert-butyl-5-hydroxy-1-methyl-1H-pyrazol-4-yl]azo}-3-hydroxy-1-naphthalenesulfonic acid;
4-[(3-ethoxy-5-hydroxy-1-(4-nitrophenyl)-1H-pyrazol-4-yl)azo]-3-hydroxy-1-naphthalenesulfonic acid;
4-{[3-tert-butyl-5-hydroxy-1-phenyl-1H-pyrazol-4-yl]azo}-3-hydroxy-1-naphthalenesulfonic acid;
3-hydroxy-4-[(5-hydroxy-3-methyl-1-pyridin-2-yl-1H-pyrazol-4-yl)azo]-1-naphthalenesulfonic acid;
4-{[1-(4-benzyloxyphenyl)-5-hydroxy-3-methyl-1H-pyrazol-4-yl]azo}-3-hydroxy-1-naphthalenesulfonic acid;
3-hydroxy-4-{[5-hydroxy-3-methyl-1-(3-trifluoromethylphenyl)-1H-pyrazol-4-yl]azo}-1-naphthalenesulfonic acid;
4-{[1-(3,4-dimethylphenyl)-5-hydroxy-3-methyl-1H-pyrazol-4-yl]azo}-3-hydroxy-1-naphthalenesulfonic acid;
3-hydroxy-4-{[5-hydroxy-3-methyl-1-(3-nitrophenyl)-1H-pyrazol-4-yl]azo}-1-naphthalenesulfonic acid;
4-{[1-(4-fluorophenyl)-5-hydroxy-3-methyl-1H-pyrazol-4-yl]azo}-3-hydroxy-1-naphthalenesulfonic acid;
3-hydroxy-4-{[5-hydroxy-1-(4-iodophenyl)-3-methyl-1H-pyrazol-4-yl]azo}-1-naphthalenesulfonic acid;
3-hydroxy-4-{[5-hydroxy-3-methyl-1-(2-nitrophenyl)-1H-pyrazol-4-yl]azo}-1-naphthalenesulfonic acid;
4-{[1-(3,4-dimethylphenyl)-3-ethoxy-5-hydroxy-1H-pyrazol-4-yl]azo}-3-hydroxy-1-naphthalenesulfonic acid;
3-hydroxy-4-{[5-hydroxy-3-methyl-1-(4-trifluoromethylphenyl)-1H-pyrazol-4-yl]azo}-1-naphthalenesulfonic acid;
3-hydroxy-4-{[5-hydroxy-3-methyl-1-(3-methylphenyl)-1H-pyrazol-4-yl]azo}-1-naphthalenesulfonic acid;
4-{[3-tert-butyl-1-(3,4-dimethylphenyl)-5-hydroxy-1H-pyrazol-yl]azo}-3-hydroxy-1-naphthalenesulfonic acid;
4-{[1-(3,4-dimethylphenyl)-5-hydroxy-3-phenyl-1H-pyrazol-4-yl]azo}-3-hydroxy-1-naphthalenesulfonic acid;
4-{[1-(3,4-Dimethylphenyl)-5-hydroxy-3-methyl-1H-pyrazol-4-yl]azo}-3-hydroxy-1-napthalenecarboxylic acid;
Methyl 5-{[1-(3,4-dimethylphenyl)-5-hydroxy-3-methyl-1H-pyrazol-4-yl]azo}-6-hydroxy-2-napthalenecarboxylate;
1-{[1-(3,4-Dimethylphenyl)-5-hydroxy-3-methyl-1H-pyrazol-4-yl]azo}-2-hydroxynaphthalene;
3-Hydroxy-4-({5-hydroxy-1-[(4-methanesulfonyl)phenyl]-3-methyl-1H-pyrazol-4-yl}azo)-1-naphthalenesulfonic acid;
4-[(1-Benzyl-5-hydroxy-3-methyl-1H-pyrazol-4-yl)azo]-3-hydroxy-1-naphthalenesulfonic acid;
4-({1-[4-(Aminosulfonyl)phenyl]-5-hydroxy-3-methyl-1H-pyrazol-4-yl}azo)-3-hydroxy-1-naphthalenesulfonic acid; and
4-[(1-tert-Butyl-5-hydroxy-3-methyl-1H-pyrazol-4-yl)azo]-3-hydroxy-1-naphthalenesulfonic acid.

By the term "protected hydroxy" or "protected —OH" as used herein, is meant the alcoholic or carboxylic—OH groups which can be protected by conventional blocking groups in the art as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "$C_5$–$C_{12}$ aryl" as used herein, unless otherwise defined, is meant a cyclic or polycyclic aromatic $C_5$–$C_{12}$ optionally containing one or two heteroatoms.

By the term "$C_6$–$C_{12}$ aryl" as used herein, unless otherwise defined, is meant phenyl, naphthyl, 3,4-methylenedioxyphenyl, pyridyl, or biphenyl.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —$(CH_2)_gC(O)OR^6$, —$S(O)_nR^7$, nitro, cyano, halogen, trifluoromethyl and protected —OH, where g is 0–6, $R^6$ is hydrogen or alkyl, n is 0–2, and $R^7$ is hydrogen or alkyl.

By the term "alkoxy" as used herein is meant —Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$–$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^6$, —$S(O)_nR^7$, nitro, cyano, halogen and protected —OH, where g is 0–6, $R^6$ is hydrogen or alkyl, n is 0–2 and $R^7$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —$CH_3$, —$CH_2$-$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$ and —$CH(CH_3)$—$CH_2$—$CH_3$, —$CH$=$CH_2$.

By the term "treating" and derivatives thereof as used herein, is meant prophylatic or therapeutic therapy.

All publications, including but not limited to patents and patent applications, cited in this specification are herein incorporated by reference as though fully set forth.

Compounds of Formula (II) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The compounds of Formula II are prepared as shown in Schemes I to III below wherein R, $R^1$, $R^2$, $R^3$, $R^4$, $R^5$, m and AR are as defined in Formula II and provided that the 'R', m and AR substituents do not include any such substituents that render inoperative the processes of Schemes I to III. All of the starting materials are commercially available or are readily made from commercially available starting materials by those of skill in the art.

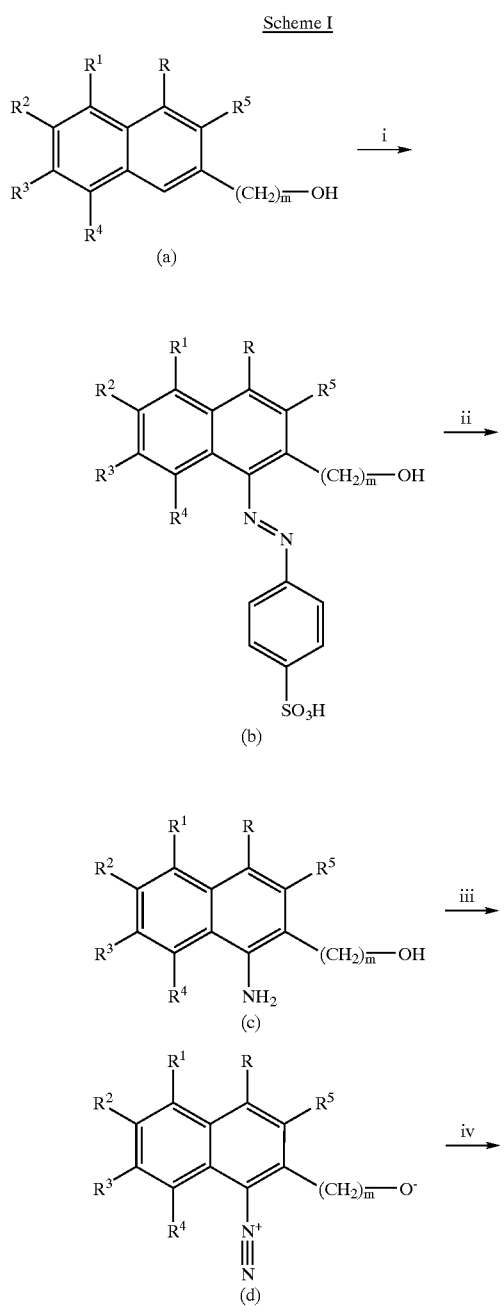

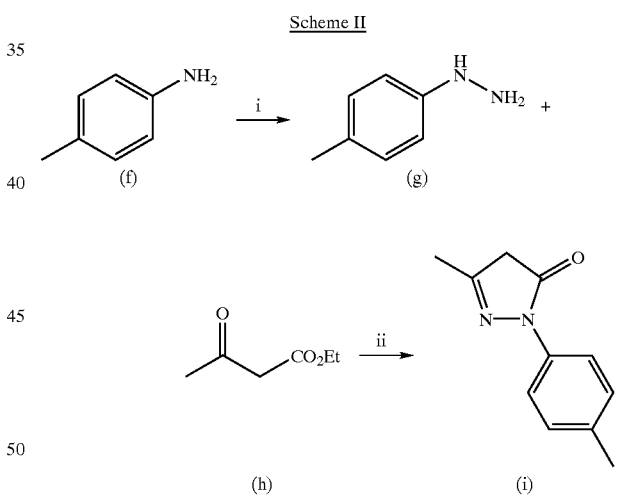

Scheme I outlines the formation of Formula II compounds. As used in scheme I the diazo compound (b) is prepared from the three hydroxy-1-napthalene compound (a) by treating (a) with 4-benzenediazonium sulfate in the presence of an appropriate base, preferably sodium hydrogen carbonate. Reduction of compound (b) with sodium hydrogen sulfite in water yielded the 4-amino-3-hydroxy-1-napthalene compound (c). Compound (c) is diazotized by reaction with sodium nitrite and an appropriate acid, such as nitric acid, sulfuric acid or, preferably hydrochloric acid, in an appropriate aqueous solvent, such as water or, preferably an ethanol-water mixture to produce diazonium compound (d). Compound (e) is prepared by reacting compound (d) in a coupling reaction with an appropriate aryl species in the presence of a base, preferably sodium hydrogen carbonate, or an acid, preferably hydrochloric acid.

Scheme II outlines the formation of pyrazoles for use in scheme I. An amine such as 4-methylaniline, compound (f), is diazotized by the action of sodium nitrite and an appropriate acid such as hydrochloric acid, nitric acid or sulfuric acid in an appropriate aqueous solvent system such as water or ethanol-water mixtures then reduced in situ by tin chloride to afford hydrazine, compound (g). The hydrazine is then condensed with a beta-keto ester such as ethyl acetoacetate, compound (h), in an appropriate solvent such as acetic acid or ethanol at an appropriate temperature typically 0–100° to give the corresponding pyrazole, compound (I) as described herein.

Scheme III

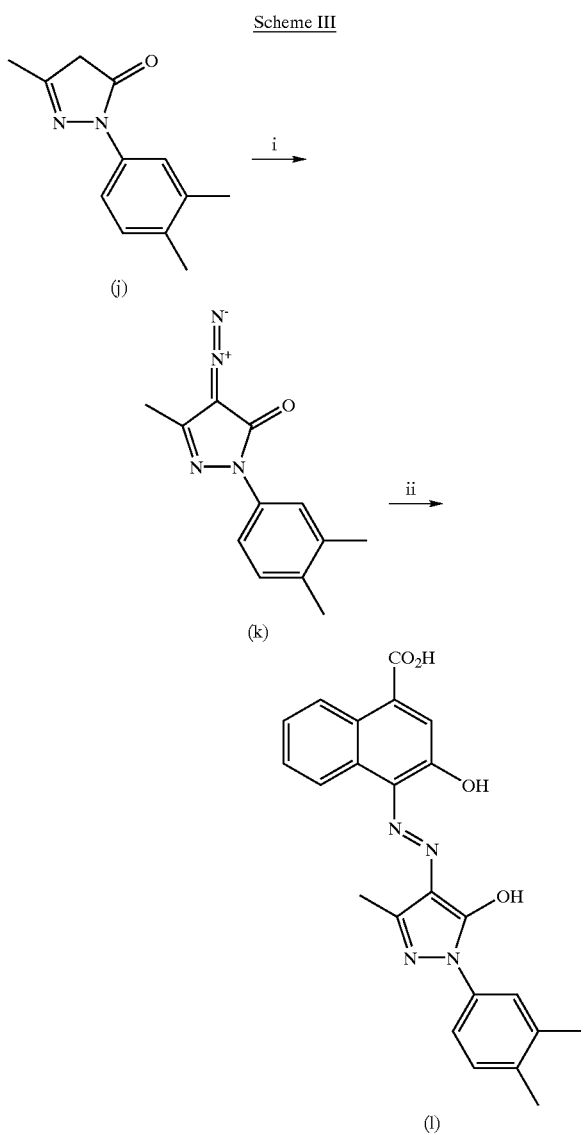

Scheme III outlines an alternative preparation of compounds of Formula II. A pyrazole (j) prepared by the method of Scheme II is treated with a sulfonyl azide such as p-toluenesulfonyl azide in the presence of a base typically triethylamine or pyridine in a suitable solvent such as ethanol, methanol or tetrahydrofuran to afford diazopyrazole (k). Compound (I) is then formed by the reaction of compound (k) in a coupling reaction with an appropriate aryl species such as naphthalene compound (a) from Scheme I in the presence of a base, typically triethylamine or sodium hydrogen carbonate, or an acid, preferably hydrochloric acid.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci., USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells in response to TPO.

Some of the most preferred compounds of this invention were also active in an in vitro proliferation assay using the murine 32D-mpl cell line (Bartley, T. D. et al., *Cell*, 1994, 77, 1117–1124). 32D-mpl cells express Tpo-R and their survival is dependent on the presence of TPO. Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al *Science*, 1997, 276, 1696–1699).

The pharmaceutically active compounds within the scope of this invention are useful as TPO mimetics in mammals, including humans, in need thereof.

Some of the preferred compounds within the scope of the invention showed activation from about 4% to 130% of control (control is the maximal response to TPO) at a concentration of 0.01–10 uM in the luciferase assay. The preferred compounds of the invention also promoted the proliferation of 32D-mpl cells at a concentration of 0.01 to 100 uM. The preferred compounds of the invention also showed activity in the CD41 megakaryocytic assay at a concentration of 0.01 to 30 uM.

The present invention therefor provides a method of treating thrombocytopenia and other conditions with depressed platelet production, which comprises administering a compound of Formula (II), as described above, in a quantity effective to enhance platelet production. The compounds of Formula (II) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (II) in the manufacture of a medicament for use as a TPO mimetic.

The invention also provides for the use of a compound of Formula (II) in the manufacture of a medicament for use in therapy.

The invention also provides for the use of a compound of Formula (II) in the manufacture of a medicament for use in enhancing platelet production.

The invention also provides for the use of a compound of Formula (II) in the manufacture of a medicament for use in treating thrombocytopenia.

The invention also provides for a pharmaceutical composition for use as a TPO mimetic which comprises a compound of Formula (II) and a pharmaceutically acceptable carrier.

The invention also provides for a pharmaceutical composition for use in the treatment of thrombocytopenia which comprises a compound of Formula (II) and a pharmaceutically acceptable carrier.

The invention also provides for a pharmaceutical composition for use in enhancing platelet production which comprises a compound of Formula (II) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents

It will be appreciated by the person of ordinary skill in the art that the compounds of Formula I and II may also exist in tautomeric forms, wherein the double bond that is drawn between the two nitrogen atoms exists between the lower nitrogen atom and the AR substituent. Tautomeric forms of the compounds of Formula I and II are exemplified by the following Formula III

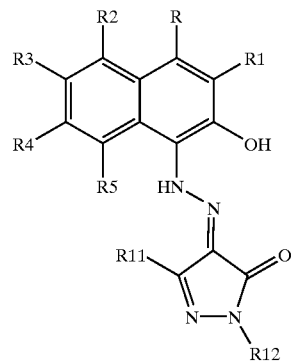

where the 'R' groups are as defined above. All such compounds are included in the scope of the invention and inherently included in the definition of the compounds of formulas I and II.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

EXAMPLE 1

Preparation of 3-hydroxy-4-[(2-hydroxy-1-naphthalenyl)azo]-1-naphthalenesulfonic acid To a stirring solution of 1-diazo-2-naphthol-4-sulfonic acid (1.49 g, 5.95 mmol) and 2-naphthol (0.858 g, 5.95 mmol) in water (20 mL), sodium bicarbonate (1.50 g, 17.85 mmol) was added slowly. The resulting solution was heated at 60° C. with stirring overnight. The solution was cooled to room temperature, and was adjusted to pH=1 with 3 N hydrochloride solution. The purple precipitate was isolated by filtration and washed with water to provide the title compound (1.35 g, 58%) MS(ES) m/z 393 [M−H].

EXAMPLE 2

Preparation of 3-hydroxy-4-[(10-hydroxy-9-phenanthrenyl)azo]-1-naphthalenesulfonic acid Following the procedure of Example 1, except substituting 9-phenathrol for 2-naphthol, the title compound was prepared as a black solid (0.048 g, 16%). MS(ES) m/z 442. [M−H].

EXAMPLE 3

Preparation of 3-hydroxy-4-[(2-hydroxy-7-methoxy-1-naphthalenyl)azo]1-naphthalenesulfonic acid Following the procedure of Example 1, except substituting 7-methoxy-2-naphthol for 2-naphthol, the title compound was prepared as a black solid (2.66 g, 74%). MS(ES) m/z 423 [M−H].

EXAMPLE 4

Preparation of 3-hydroxy-4-[(4-hydroxy-2-methoxy-1-naphthalenyl)azo]-1-naphthalenesulfonic acid a) 3-methoxy-1-naphthol To a stirring solution of 1,3-dihydroxynaphthalene (2.31 g, 14.4 mmol) in methanol (150 mL) at 0° C., hydrochloride gas was bubbed for 10 min. The resulting solution was continued stirring at room temperature for 24 hrs. A residue was obtained after evaporation of methanol and purified by silica gel column chromatography eluted with chloroform to provide the title compound as purple crystals (1.42 g, 57%). $^1$H NMR(300 MHz CDCl3) δ8.08(d, 1H), 7.70(d, 1H), 7.46(t, 1H), 7.34(t, 1H), 6.78 (s, 1H), 6.54 (s, 1H), 5.61(s, 1H), 3.90(s, 3H).

b) 3-Hydroxy-[4-(4-hydroxy-2-methoxy-1-naphthalenyl)azo]-1-naphthalenesulfonic acid Following the procedure of Example 1, except substituting 3-methoxy-1-naphthol for 2-naphthol, the title compound was prepared as a black solid (2.37 g, 88%). MS(ES) m/z 423 [M−H].

EXAMPLE 5

3-Hydroxy-4-[(2-hydroxy-1-naphthalenyl)azo]-7-nitro-1-naphthalenesulfonic acid

The title compound is commercially available from Pfaltz and Bauer, Waterbury, Conn. and used as provided. MS(ES) m/z 438 [M−H].

EXAMPLE 6

3-Hydroxy-4-[(1-hydroxy-2-naphthalenyl)azo]-7-nitro-1-naphthalenesulfonic acid, monosodium salt The title compound is commercially available from the Aldrich Chemical Company, Milwaukee, Wis. and used as provided. MS(ES) m/z 438 [M−H].

EXAMPLE 7

3-Hydroxy-4-[(1-hydroxy-2-naphthalenyl)azo]-1-naphthalenesulfonic acid

The title compound is commercially available from Aldrich Chemical Company, Milwaukee, Wis. and used as provided. MS(ES) m/z 393 [M−H].

EXAMPLE 8

3-Hydroxy-4-[(2-hydroxy-5-methyl-1-phenyl)azo]-1-naphthalenesulfonic acid

The title compound is commercially available Aldrich Chemical Company, Milwaukee, Wis. and used as provided. MS(ES) m/z 357 [M−H].

EXAMPLE 9

Preparation of 3-hydroxy-4-[(5-hydroxy-3-methyl-1-phenyl-1H-pyrazol-4-yl)azo]-1-naphthalenesulfonic acid, monosodium salt Following the procedure of Example 1, except substituting 3-methyl-1-phenyl-3-pyrazolin-5-one for 2-naphthol, the title compound was prepared as a red solid 3.82 g; 90%). MS(ES) m/z 423 [M−H].

EXAMPLE 10

Preparation of 4-[(1,3-dimethyl-5-hydroxy-1H-pyrazol-4-yl)azo]-3-hydroxy-1-naphthalenesulfonic acid, monohydrate, monosodium salt Following the procedure of Example 1, except substituting 1,3-dimethyl-3-pyrazolin-5-one for 2-naphthol, the title compound was prepared as a red solid 1.95 g; 49%). Anal ($C_{15}H_{14}N_4OS.Na.H_2O$) calcd: C, 44.8; H, 4.0; N, 13.9. found: C, 44.6; H, 3.7; N, 13.7.

EXAMPLE 11

Preparation of 3-hydroxy-4-{[5-hydroxy-1-(4-methylphenyl)-3-methyl-1H-pyrazol-4-yl]azo}-1-naphthalenesulfonic acid Following the procedure of Example 1, except substituting 3-methyl-1-(4-methylphenyl)-3-pyrazolin-5-one for 2-naphthol, the title compound was prepared as a red solid (2.1 g; 81%). MS(ES) m/z 436.9 [M−H].

EXAMPLE 12

Preparation of 4-{[1-(4-chlorophenyl)-5-hydroxy-3-methyl-1H-pyrazol-4-yl]azo}-3-hydroxy-1-naphthalenesulfonic acid Following the procedure of Example 1, except substituting 1-(4-chlorophenyl)-3-methyl-3-pyrazolin-5-one for 2-naphthol, the title compound was prepared as a red solid (1.8 g; 97%). MS(ES) m/z 456.7 [M−H].

EXAMPLE 13

Preparation of 4-{[(3-chlorophenyl)-5-hydroxy-3-methyl-1H-pyrazol-4-yl]azo}-3-hydroxy-1-naphthalenesulfonic acid Following the procedure of Example 1, except substituting 1-(3-chlorophenyl)-3-methyl-3-pyrazolin-5-one for 2-naphthol, the title compound was prepared as a red solid (0.69 g; 50%). MS(ES) m/z 456.7 [M−H].

EXAMPLE 14

Preparation of 3-hydroxy-4-[(5-hydroxy-3-methyl-1-phenyl-1H-pyrazol-4-yl)azo]-1-naphthalenecarboxylic acid a) 3-Nitro-1-napthalenecarboxylic acid A mixture of 3-nitro-1,8-napthalic anhydride (100 g, 0.411 mol.) and sodium hydroxide (55.8 g; 1.4 mol.) in water (2 L) was added to a suspension of mercury (I) oxide (96.8 g; 0.447 mol.) in water (270 mL) and glacial acetic acid (200 mL). The mixture which frothed vigorously was then stirred and heated under reflux for 3 days. The suspension was then hot-filtered and the insoluble residue dried in vacuo at 70° for 3 days to give a yellow powder (169.7 g). This solid was suspended in a mixture of concentrated hydrochloric acid (500 mL) and water (1 L) and stirred and heated under reflux for 4 h. Hot-filtration gave crude 3-nitronapthalene-1-carboxylic acid (92.3 g) which was recrystallised from glacial acetic acid with hot-filtration to remove some insoluble material to afford the title compound (36.4 g) as a cream, crystalline solid. mp 255–257°.

b) 3-Amino-1-napthalenecarboxylic acid, sodium salt

A suspension of the compound from example 14 a) (10.0 g; 0.046 mol.) in ethanol (100 mL) was treated with 10% aqu. sodium hydroxide (16.6 mL; 0.046 mol.) and water (20.0 mL) and stirred until all solids had dissolved. This solution was then hydrogenated over 10% w/w palladium-on-charcoal (2.0 g) at room temperature and 50 p.s.i. for 4 h. The solution was filtered and evaporated to afford the title compound (8.65 g; 90%) as a yellow solid. MS(ES) m/z 188 [M+H].

c) 3-Hydroxy-1-napthalenecarboxylic acid

A solution of the compound from example 14 b) (8.73 g; 0.042 mol.) in water (300 mL) was treated with 2M aqu. sulfuric acid (60.0 mL) to precipitate the free acid as a fine powder. This suspension was then stirred and cooled to 10° then slowly treated dropwise with a solution of sodium nitrite (3.03 g; 0.044 mol.) in water (30.0 mL). After 30 min. at 10° the solution was added very slowly dropwise to a refluxing solution of 40% aqu. sulfuric acid (1 L). Complete addition took ~1 h. After complete addition the mixture was heated under reflux for a further 15 min. then quickly hot-filtered through a plug of glass wool to remove insoluble, charred material. The filtrate was allowed to cool depositing the title compound (5.85 g; 74%) as yellow crystals. mp 210–212°. MS(ES) m/z 187 [M–H].

d) 4-Amino-3-hydroxy-1-naphthalenecarboxylic acid

To a stirred solution of p-benzenediazonium sulfonate, which was prepared by the addition of sodium sulfanilate (0.525 g, 2.7 mmole) to sodium nitrite at 0°, and the compound from example 14 c) (0.413 g, 2.2 mmol) in water (20 mL), sodium bicarbonate (2.3 g, 27.0 mmol) was added slowly. The resulting solution was heated at 60° C. with stirring overnight. After the solution was cooled to 50° C., sodium hydrogen sulfite (1.05 g, 6.0 mmole) was added. The resulting solution was stirred for 30 min. at 50° C. After cooling down to room temperature, the solid was removed by filtration. The filtrate was evaporated to dryness and the residue was purified by flash chromatography (silica gel, 45% dichloromethane/45% ethyl acetate/10% methanol) to give the title compound (0.066 g, 15%) MS(ES) m/z 203.8 [M+H].

e) 3-Hydroxy-4-[(5-hydroxy-3-methyl-1-phenyl-1H-pyrazol-4-yl)azo]-1-naphthalenecarboxylic acid To a stirred solution of the compound from example 14 d) (0.203 g, 1.0 mmol) in ethanol (1.0 ml), ice (1.0 g) and hydrochloric acid (37%, 0.3 ml), was added a solution of sodium nitrite (0.083 g, 1.2 mmol) in water (0.2 ml). After the resulting solution was stirred at room temperature for 30 min, 3-methyl-1-phenyl-3-pyrazolin-5-one (0.174 g, 1.0 mmole) was added. Sodium bicarbonate (0.84 g, 10 mmole) was added slowly into the reaction mixture and the resulting solution was heated at 60° C. with stirring overnight. A red precipitate was obtained by adding 3N HCl solution which was purified by chromatography [ODS, step gradient, 10–90% acetonitrile/water (0.1% TFA)] to give the title compound (0.021 g, 5%) MS(ES) m/z 386.9 [M–H].

EXAMPLE 15

Preparation of 3-hydroxy-4-{[5-hydroxy-3-methyl-1-(4-methylphenyl)-1H-pyrazol-4-yl]azo}-1-napthalenecarboxylic acid Following the procedure of Example 14 e), except substituting 3-methyl-1-(4-methylphenyl)-3-pyrazolin-5-one for 3-methyl-1-phenyl-3-pyrazolin-5-one, the title compound was prepared as a red solid (0.004 g). MS(ES) m/z 402.6 [M–H].

EXAMPLE 16

Preparation of 3-hydroxy-4-{{5-hydroxy-1-[3-(N-ethylsulfonamido)phenyl]-3-methyl-1H-pyrazol-4-yl}azo}-1-naphthalenesulfonic acid Following the procedure of Example 1, except substituting [3-(N-ethylsulfonamido)phenyl]-3-methyl-3-pyrazolin-5-one for 2-naphthol, the title compound was prepared as a red solid (). MS(ES) m/z.530 [M–H].

EXAMPLE 17

Preparation of 4-[(3-ethoxycarbonyl-5-hydroxy-1-phenyl-1H-pyrazol-4-yl)azo]-3-hydroxy-1-naphthalenesulfonic acid;

Following the procedure of Example 1, except substituting 3-ethoxycarbonyl-1-phenyl-3-pyrazolin-5-one for 2-naphthol, the title compound was prepared as a red solid (). MS(ES) m/z481 [M–H].

EXAMPLE 18

Preparation of 3-hydroxy-4-{[5-hydroxy-3-methyl-1-(4-nitrophenyl)-1H-pyrazol-4-yl]azo}-1-naphthalenesulfonic acid Following the procedure of Example 1, except substituting 3-methyl-1-(4-nitrophenyl)-3-pyrazolin-5-one for 2-naphthol, the title compound was prepared as a red solid (2.0 g; 99%). MS(ES) m/z 468 [M–H].

EXAMPLE 19

Preparation of 4-{[3-tert-butyl-5-hydroxy-1-methyl-1H-pyrazol-4-yl]azo}-3-hydroxy-1-naphthalenesulfonic acid Following the procedure of Example 1, except substituting 3-tert-butyl-1-methyl-3-pyrazolin-5-one for 2-naphthol, the title compound was prepared as a red solid solid (1.4 g; 82%). MS(ES) m/z 403 [M–H].

EXAMPLE 20

Preparation of 4-[(3-ethoxy-5-hydroxy-1-(4-nitrophenyl)-1H-pyrazol-4-yl)azo]-3-hydroxy-1-naphthalenesulfonic acid Following the procedure of Example 1, except substituting 3-ethoxy-1-(4-nitrophenyl)-3-pyrazolin-5-one for 2-naphthol, the title compound was prepared as a red solid (1.9 g; 89%). MS(ES) m/z 498 [M–H].

EXAMPLE 21

Preparation of 4-{[3-tert-butyl-5-hydroxy-1-phenyl-1H-pyrazol-4-yl]azo}-3-hydroxy-1-naphthalenesulfonic acid Following the procedure of Example 1, except substituting 3-tert-butyl-1-phenyl-3-pyrazolin-5-one for 2-naphthol, the title compound was prepared as a red solid (1.1 g; 55%). MS(ES) m/z 465 [M–H].

EXAMPLE 22

Preparation of 3-hydroxy-4-[(5-hydroxy-3-methyl-1-pyridin-2-yl-1H-pyrazol-4-yl)azo]-1-naphthalenesulfonic acid, a) 3-Methyl-1-pyridin-2-yl-3-pyrazolin-5-one A solution of 2-hydrazinopyridine (1.35 g; 0.012 mol.) and ethyl acetoacetate (1.60 mL; 0.012 mol.) in glacial acetic acid (50.0 mL) was stirred and heated at 100° for 24 h.

The solvent was evaporated and the product purified by chromatography (silica gel, 50% ethyl acetate/hexanes) to afford the title compound (0.78 g; 37%) as a colorless solid. MS(ES) m/z 176 [M+H].

b) 3-hydroxy-4-[(5-hydroxy-3-methyl-1-pyridin-2-yl-1H-pyrazol-4-yl)azo]-1-naphthalenesulfonic acid Following the procedure of Example 1, except the compound from Example 22a) 2-naphthol, the title compound was prepared as a red solid (1.33 g; 73%). MS(ES) m/z 424 [M–H].

EXAMPLE 23

Preparation of 4-{[1-(4-benzyloxyphenyl)-5-hydroxy-3-methyl-1H-pyrazol-4-yl]azo}-3-hydroxy-1-naphthalenesulfonic acid a) 4-Benzyloxyphenylhydrazine A solution of 4-benzyloxyaniline hydrochloride (11.3 g; 0.048 mole) in concentrated hydrochloric acid (40.0 mL) was cooled to 0° then treated dropwise with a solution of sodium nitrite (3.28 g; 0.048 mole) in water (20.0 mL). The mixture was stirred 0° for a further 10 min. then poured into a cold (−10°) solution of tin dichloride hydrate (40.0 g; 0.18 mole) in concentrated hydrochloric acid (40.0 mL). The mixture was allowed to warm to room temperature with stirring for 1 h.

The mixture was basified with 10% aqu. sodium hydroxide, ethyl acetate (1 L) was added and the mixture filtered to remove unwanted tin residues. The organic layer was then dried and evaporated to afford the title compound as a yellow solid (6.9 g; 67%). mp 105–107°.

b) 1-(4-Benzyloxyphenyl)-3-methyl-3-pyrazolin-5-one

Following the procedure of Example 22a), except the compound from Example 23a) for 2-hydrazinopyridine, the title compound was prepared (1.6 g; 60%). MS(ES) m/z 281 [M+H].

c) 4-{[1-(4-Benzyloxyphenyl)-5-hydroxy-3-methyl-1H-pyrazol-4-yl]azo}-3-hydroxy-1-naphthalenesulfonic acid Following the procedure of Example 1, except the compound from Example 23b) for 2-naphthol, the title compound was prepared as a red solid (2.8 g; 98%). MS(ES) m/z 529 [M–H].

EXAMPLE 24

Preparation of 3-hydroxy-4-{[5-hydroxy-3-methyl-1-(3-trifluoromethylphenyl)-1H-pyrazol-4-yl]azo}-1-naphthalenesulfonic acid a) 3-Methyl-1-(3-trifluoromethylphenyl)-3-pyrazolin-5-one Following the procedure of Example 22a), except substituting 3-trifluoromethylphenylhydrazine for 2-hydrazinopyridine, the title compound was prepared (0.78 g; 76%). MS(ES) m/z 243 [M+H].

b) 3-Hydroxy-4-{[5-hydroxy-3-methyl-1-(3-trifluoromethylphenyl)-1H-pyrazol-4-yl]azo}-1-naphthalenesulfonic acid Following the procedure of Example 1, except substituting the compound from Example 24a) for 2-naphthol, the title compound was prepared as a red solid (1.19 g; 78%). MS(ES) m/z 491 [M–H].

EXAMPLE 25

Preparation of 4-{[1-(3,4-dimethylphenyl)-5-hydroxy-3-methyl-1H-pyrazol-4-yl]azo}-3-hydroxy-1-naphthalenesulfonic acid a) 1-(3,4-Dimethylphenyl)-3-methyl-3-pyrazolin-5-one Following the procedure of Example 22a), except substituting 3,4-dimethylphenylhydrazine for 2-hydrazinopyridine, the title compound was prepared (16.8 g; 64%). MS(ES) m/z 203 [M+H].

b) 4-{[1-(3,4-Dimethylphenyl)-5-hydroxy-3-methyl-1H-pyrazol-4-yl]azo}-3-hydroxy-1-naphthalenesulfonic acid Following the procedure of Example 1, except substituting the compound from Example 25a) for 2-naphthol, the title compound was prepared as a red solid (23.3 g; 97%). MS(ES) m/z 451 [M–H].

EXAMPLE 26

Preparation of 3-hydroxy-4-{[5-hydroxy-3-methyl-1-(3-nitrophenyl)-1H-pyrazol-4-yl]azo}-1-naphthalenesulfonic acid a) 3-Methyl-1-(3-nitrophenyl)-3-pyrazolin-5-one Following the procedure of Example 22a), except substituting 3-nitrophenylhydrazine for 2-hydrazinopyridine, the title compound was prepared (3.16 g; 98%). MS(ES) m/z 220 [M+H].

b) 3-Hydroxy-4-{[5-hydroxy-3-methyl-1-(3-nitrophenyl)-1H-pyrazol-4-yl]azo}-1-naphthalenesulfonic acid Following the procedure of Example 1, except substituting the compound from Example 26a) for 2-naphthol, the title compound was prepared as a red solid (2.4 g; 92%). MS(ES) m/z 468 [M–H].

EXAMPLE 27

Preparation of 4-{[1-(4-fluorophenyl)-5-hydroxy-3-methyl-1H-pyrazol-4-yl]azo}-3-hydroxy-1-naphthalenesulfonic acid a) 1-(4-Fluorophenyl)-3-methyl-3-pyrazolin-5-one Following the procedure of Example 22a), except substituting 4-fluorophenylhydrazine for 2-hydrazinopyridine, the title compound was prepared (2.2 g; 75%). MS(ES) m/z 193 [M+H].

b) 3-Hydroxy-4-{[1-(3-fluorophenyl)-5-hydroxy-3-methyl-1H-pyrazol-4-yl]azo}-1-naphthalenesulfonic acid Following the procedure of Example 1, except substituting the compound from Example 27a) for 2-naphthol, the title compound was prepared as a red solid (2.03 g; 75%). MS(ES) m/z 441 [M–H].

EXAMPLE 28

Preparation of 3-hydroxy-4-{[5-hydroxy-1-(4-iodophenyl)-3-methyl-1H-pyrazol-4-yl]azo}-1-naphthalenesulfonic acid a) 1-(4-Iodophenyl)-3-methyl-3-pyrazolin-5-one Following the procedure of Example 22a), except substituting 4-iodophenylhydrazine for 2-hydrazinopyridine, the title compound was prepared (0.60 g; 17%). MS(ES) m/z 301 [M+H].

b) 3-Hydroxy-4-{[5-hydroxy-3-methyl-1-(3-nitrophenyl)-1H-pyrazol-4-yl]azo}-1-naphthalenesulfonic acid Following the procedure of Example 1, except substituting the compound from Example 28a) for 2-naphthol, the title compound was prepared as a red solid (0.50 g; 45%). MS(ES) m/z 549 [M–H].

EXAMPLE 29

Preparation of 3-hydroxy-4-{[5-hydroxy-3-methyl-1-(2-nitrophenyl)-1H-pyrazol-4-yl]azo}-1-naphthalenesulfonic acid a) 3-Methyl-1-(2-nitrophenyl)-3-pyrazolin-5-one Following the procedure of Example 22a), except substituting 2-nitrophenylhydrazine for 2-hydrazinopyridine, the title compound was prepared (1.84 g; 45%). MS(ES) m/z 261 [M+CH$_3$CN+H].

b) 3-Hydroxy-4-{[5-hydroxy-3-methyl-1-(2-nitrophenyl)-1H-pyrazol-4-yl]azo}-1-naphthalenesulfonic acid Following the procedure of Example 1, except substituting the compound from Example 29a) for 2-naphthol, the title compound was prepared as a red solid (0.067 g; 5%). MS(ES) m/z 468 [M–H].

EXAMPLE 30

Preparation of 4-{[1-(3,4-dimethylphenyl)-3-ethoxy-5-hydroxy-1H-pyrazol-4-yl]azo}-3-hydroxy-1-naphthalenesulfonic acid a) 1-(3,4-Dimethylphenyl)-1H,4H-pyrazolin-3,5-dione A solution of 3,4-dimethylphenylhydrazine (8.15 g; 0.06 mol.) and diethyl malonate (11.5 g; 0.072 mol.) in anhydrous toluene (40.0 mL) was treated with sodium hydride (60%, pre-washed with hexanes) (0.45 g; 0.072 mol.) and heated under reflux with stirring and with removal of water through use of a Dean-Stark apparatus for 4 h.

Ethyl acetate and water were added and the mixture filtered to remove insoluble impurities. The bi-phasic filtrate was then acidified with 3M aqu. hydrochloric acid and filtered to afford the title compound (1.0 g; 8%) as an orange powder. MS(ES) m/z 205 [M+H].

b) 1-(3,4-Dimethylphenyl)-3-ethoxy-3-pyrazolin-5-one

A solution of the compound from Example 30a) (0.315 g; 1.5 mmol.) in ethanol (15.0 mL) was treated with 3 drops of concentrated sulfuric acid then heated under reflux with stirring and with removal of water through use of a Dean-Stark apparatus containing 3 Å molecular sieves for 24 h.

The reaction was cooled and quenched by addition of water. The mixture was then evaporated to give a solid which was purified by chromatography (silica gel, step gradient, 0–2% methanol/chloroform) to afford the title compound (0.172 g; 48%) as a yellow solid. MS(ES) m/z 233 [M+H].

c) 4-{[1-(3,4-Dimethylphenyl)-3-ethoxy-5-hydroxy-1H-pyrazol-4-yl]azo}-3-hydroxy-1-naphthalenesulfonic acid Following the procedure of Example 1, except substituting the compound from Example 30b) for 2-naphthol, the title compound was prepared as a red solid (60 mg; 26%). MS(ES) m/z 481 [M–H].

EXAMPLE 31

Preparation of 3-hydroxy-4-{[5-hydroxy-3-methyl-1-(4-trifluoromethylphenyl)-1H-pyrazol-4-yl]azo}-1-naphthalenesulfonic acid a) 3-Methyl-1-(4-trifluoromethylphenyl)-3-pyrazolin-5-one Following the procedure of Example 22a), except substituting 4-trifluoromethylphenylhydrazine for 2-hydrazinopyridine, the title compound was prepared (3.25 g; 93%). MS(ES) m/z 243 [M+H].

b) 3-Hydroxy-4-{[5-hydroxy-3-methyl-1-(3-nitrophenyl)-1H-pyrazol-4-yl]azo}-1naphthalenesulfonic acid Following the procedure of Example 1, except substituting the compound from Example 31a) for 2-naphthol, the title compound was prepared as a red solid (1.64 g; 77%). MS(ES) m/z 491 [M–H].

EXAMPLE 32

Preparation of 3-hydroxy-4-{[5-hydroxy-3-methyl-1-(3-methylphenyl)-1H-pyrazol-4-yl]azo}-1-naphthalenesulfonic acid a) 3-Methyl-1-(3-methylphenyl)-3-pyrazolin-5-one Following the procedure of Example 22a), except substituting 3-methylphenylhydrazine for 2-hydrazinopyridine, the title compound was prepared (2.82 g; 90%). MS(ES) m/z 189 [M+H].

b) 3-Hydroxy-4-{[5-hydroxy-3-methyl-1-(3-methylphenyl)-1H-pyrazol-4-yl]azo}-1-naphthalenesulfonic acid Following the procedure of Example 1, except substituting the compound from Example 32a) for 2-naphthol, the title compound was prepared as a red solid (1.2 g; 49%). MS(ES) m/z 437 [M–H].

EXAMPLE 33

Preparation of 4-{[3-tert-butyl-1-(3,4-dimethylphenyl)-5-hydroxy-1H-pyrazol-4-yl]azo}-3-hydroxy-1-naphthalenesulfonic acid a) 3-tert-Butyl-1-(3,4-dimethylphenyl)-3-pyrazolin-5-one Following the procedure of Example 22a), except substituting 3,4-dimethylphenylhydrazine for 2-hydrazinopyridine and ethyl tert-butylacetate for ethyl acetoacetate, the title compound was prepared (25.1 g; 99%). MS(ES) m/z 245 [M+H].

b) 4-{[3-tert-Butyl-1-(3,4-dimethylphenyl)-5-hydroxy-1H-pyrazol-4-yl]azo}-3-hydroxy-1-naphthalenesulfonic acid Following the procedure of Example 1, except substituting the compound from Example 25a) for 2-naphthol, the title compound was prepared as a red solid 3.4 g; 84%). MS(ES) m/z 493 [M–H].

EXAMPLE 34

Preparation of 4-{[1-(3,4-dimethylphenyl)-5-hydroxy-3-phenyl-1H-pyrazol-4-yl]azo}-3-hydroxy-1-naphthalenesulfonic acid a) 1-(3,4-Dimethylphenyl)-3-phenyl-3-pyrazolin-5-one Following the procedure of Example 22a), except substituting 3,4-dimethylphenylhydrazine for 2-hydrazinopyridine and ethyl benzoylacetate for ethyl acetoacetate, the title compound was prepared (16.0 g; 61%). MS(ES) m/z 265 [M+H].

b) 4-{[1-(3,4-Dimethylphenyl)-5-hydroxy-3-phenyl-1H-pyrazol-4-yl]azo}-3-hydroxy-1-naphthalenesulfonic acid Following the procedure of Example 1, except substituting the compound from Example 25a) for 2-naphthol, the title compound was prepared as a red solid (2.1 g; 34%). MS(ES) m/z 513 [M–H].

EXAMPLE 35

Preparation of 4-{[1-(3,4-dimethylphenyl)-5-hydroxy-3-methyl-1H-pyrazol-4-yl]azo}-3-hydroxy-1-napthalenecarboxylic acid a) 4-Diazo-1-(3,4-dimethylphenyl)-3-methyl-3-pyrazolin-5-one A methanol solution of the compound of Example 25a) (0.85 g, 4.19 mmol) and tosyl azide (0.84 g, 4.19 mmol) was treated with triethylamine (0.42 g, 4.19 mmol). The reaction was stirred at room temperature for 2 hours. It was concentrated and applied to a silica gel column and washed with ethylacetate and hexanes to give the title compound as yellow powder (0.5 g, 53%). MS(ES) m/z 229 [M+H]$^+$. HPLC $t_R$ 7.2 min [Ultrasphere® ODS, 4.6×250 mm, 2 mL/min, gradient 20–90% acetonitrile/water (0.1% TFA) during 12 min, UV detection at 254 nM].

b) 4-{[1-(3,4-Dimethylphenyl)-5-hydroxy-3-methyl-1H-pyrazol-4-yl]azo}-3-hydroxy-1-napthalenecarboxylic acid To a solution of the compound from Example 14c) (0.030 g, 0.13 mmol) and the compound from Example 35a) (27 mg, 0.13 mmol) in ethanol (3.0 mL) was added triethylamine (0.30 mL). The reaction was stirred at room temperature for 7d. The solution was concentrated and acidified with 1N HCl. The precipitate was filtered and purified by chromatography [ODS, step gradient, 10–90% acetonitrile/water (0.1% TFA)] to give the title compound as red powder (0.020 g, 36%). MS(ES) m/z 431 [M+H]⁺, HPLC $t_R$ 6.9 min [Ultrasphere® ODS, 4.6×250 mm, 2 mL/min, gradient 20–90% acetonitrile/water (0.1% TFA) during 11 min, UV detection at 254 nM].

EXAMPLE 36

Preparation of methyl 5-{[1-(3,4-dimethylphenyl)-5-hydroxy-3-methyl-1H-pyrazol-4-yl]azo}-6-hydroxy-2-napthalenecarboxylate Following the procedure of Example 35b) except substituting methyl 6 hydroxy-2-naphthalenecarboxylate for 3-hydroxy-1-naphthalenecarboxylic acid, the title compound was prepared as red powder (0.020 g, 36%). MS(ES) m/z 431 [M+H]⁺, HPLC $t_R$ 10.4 min [Ultrasphere® ODS, 4.6×250 mm, 2 mL/min, gradient 40–90% acetonitrile/water (0.1% TFA) during 11 min, UV detection at 254 nM].

EXAMPLE 37

Preparation of 1-{[1-(3,4-dimethylphenyl)-5-hydroxy-3-methyl-1H-pyrazol-4-yl]azo}-2hydroxynaphthalene Following the procedure of Example 35b) except substituting 2-hydroxynaphthalene for 3-hydroxy-1-naphthalenecarboxylic acid, the title compound was prepared as red powder (0.039 g, 70%). MS(ES) m/z 373 [M+H]⁺, HPLC $t_R$ 10.8 min [Ultrasphere® ODS, 4.6×250 mm, 2 mL/min, gradient 40–90% acetonitrile/water (0.1 % TFA) during 11 min, UV detection at 254 nM].

EXAMPLE 38

Preparation of 3-hydroxy-4-({5-hydroxy-1-[(4-methanesulfonyl)phenyl]-3-methyl-1H-pyrazol-4-yl}azo)-1-naphthalenesulfonic acid a) 1-(4-Methanesulfonylphenyl)-3-methyl-3-pyrazolin-5-one Following the procedure of Example 22a), except substituting 4-methanesulfonylphenylhydrazine for 2-hydrazinopyridine, the title compound was prepared (1.1 g; 50%). MS(ES) m/z 253 [M+H]⁺.

b) 3-Hydroxy-4-({5-hydroxy-1-[(4-methanesulfonyl)phenyl]-3-methyl-1H-pyrazol-4-yl}azo)-1-naphthalenesulfonic acid Following the procedure of Example 1, except substituting the compound from Example 38a) for 2-naphthol, the title compound was prepared as a red solid (0.158 g; 17%). MS(ES) m/z 501 [M–H]⁻.

EXAMPLE 39

Preparation of 4-[(1-benzyl-5-hydroxy-3-methyl-1H-pyrazol-4-yl)azo]-3-hydroxy-1-naphthalenesulfonic acid a) 1-Benzyl-3-methyl-3-pyrazolin-5-one Following the procedure of Example 22a), except substituting benzylhydrazine for 2-hydrazinopyridine, the title compound was prepared (0.74 g; 77%). MS(ES) m/z 189 [M+H]⁺.

b) 4-[(1-Benzyl-5-hydroxy-3-methyl-1H-pyrazol-4-yl)azo]-3-hydroxy-1-naphthalenesulfonic acid Following the procedure of Example 1, except substituting the compound from Example 39a) for 2-naphthol, the title compound was prepared as a red solid (0.07 g; 30%). MS(ES) m/z 437 [M–H]⁻.

EXAMPLE 40

Preparation of 4-({1-[4-(aminosulfonyl)phenyl]-5-hydroxy-3-methyl-1H-pyrazol-4-yl}azo)-3-hydroxy-1-naphthalenesulfonic acid a) 1-[4-(Aminosulfonyl)phenyl]-3-methyl-3-pyrazolin-5-one Following the procedure of Example 22a), except substituting (4-aminosulfonyl)phenylhydrazine for 2-hydrazinopyridine, the title compound was prepared (0.1.26 g; 74%). MS(ES) m/z 254 [M+H]⁺.

b) 4-({1-[4(Aminosulfonyl)phenyl]-5-hydroxy-3-methyl-1H-pyrazol-4-yl}azo)-3-hydroxy-1-naphthalenesulfonic acid Following the procedure of Example 1, except substituting the compound from Example 40a) for 2-naphthol, the title compound was prepared as a red solid (0.101 g; 34%). MS(ES) m/z 502 [M–H]⁻.

EXAMPLE 41

Preparation of 4-[(1-tert-butyl-5-hydroxy-3-methyl-1H-pyrazol-4-yl)azo]-3-hydroxy-1-naphthalenesulfonic acid a) 1-tert-Butyl-3-methyl-3-pyrazolin-5-one Following the procedure of Example 22a), except substituting tert-butylhydrazine for 2-hydrazinopyridine, the title compound was prepared (0.90 g; 73%). MS(ES) m/z 155 [M+H]⁺.

b) 4-[(1-tert-Butyl-5-hydroxy-3-methyl-1H-pyrazol-4-yl)azo]-3-hydroxy-1-naphthalenesulfonic acid Following the procedure of Example 1, except substituting the compound from Example 41a) for 2-naphthol, the title compound was prepared as a red solid (0.0663 g; 24%). MS(ES) m/z 403 [M–H]⁻.

EXAMPLE 42

Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
| --- | --- |
| 3-hydroxy-4-[(4-hydroxy-2-methoxy-1-naphthalenyl)azo]-1-naphthalenesulfonic acid (Compound 1) | 25 mg |
| Lactose | 55 mg |
| Talc | 16 mg |
| Magnesium Stearate | 4 mg |

EXAMPLE 43

Injectable Parenteral Composition

An injectable form for administering a presently invented agonist of the TPO receptor is produced by stirring 1.5% by weight of 3-hydroxy-4[-(5-hydroxy-3-methyl-1-phenyl-1H-pyrazol-4-yl)azo]-1-naphthalenesulfonic acid, monosodium salt (Compound 2) in 10% by volume propylene glycol in water.

EXAMPLE 44

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 3-hydroxy-4-{[5-hydroxy-3-methyl-1-(4-methylphenyl)-1H-pyrazol-4-yl]azo}-1-napthalenecarboxylic acid (Compound 3) | 20 mg |
| calcium sulfate dihydrate | 30 mg |
| sucrose | 4 mg |
| starch | 2 mg |
| talc | 1 mg |
| stearic acid | 0.5 mg |

Preferred among the compounds of the Examples are compounds of Examples 9, 23, 27, 32 and 33.

Most preferred among the compounds of the Examples are compounds of Examples 24, 25, 28, 30 and 31.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating of thrombocytopenia in a mammal in need thereof which comprises administering to such mammal a therapeutically effective amount of a compound of Formula (II)

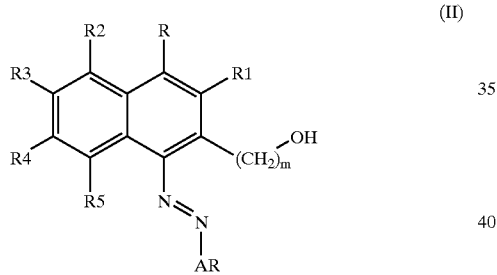

(II)

wherein:
R, $R^1$, $R^2$, $R^3$, $R^4$ and $R^5$ are each independently selected from hydrogen, —C(O)$OR^6$, —CONR$^9$R$^{10}$, —SO$_2$NR$^9$R$^{10}$, phosphonic acid, phosphinic acid, $C_{1-6}$alkyl, $C_{1-6}$alkoxy, —(CH$_2$)$_p$OR$^6$, nitro, cyano, halogen, —NR$^9$R$^{10}$, N-acylamino, N-sulfonylamino, —S(O)$_n$R$^6$, $C_5$–$C_{12}$aryl, substituted $C_5$–$C_{12}$aryl, alkyl, cycloalkyl, substituted cycloalkyl, protected —OH, and alkyl substituted with one or more substituents selected from the group consisting of alkoxy, acyloxy, $C_5$–$C_{12}$aryl, substituted $C_5$–$C_{12}$aryl, —NR$^9$R$^{10}$, N-acylamino, oxo, hydroxy, cycloalkyl, substituted cycloalkyl, —C(O)$OR^6$, —C(O)NR$^9$R$^{10}$, —S(O)$_2$NR$^9$R$^{10}$, —S(O)$_n$R$^6$, aryloxy, nitro, cyano, halogen, and protected —OH; where
n is 0 to 3;
p is 0–6;
$R^6$ is selected from hydrogen, alkyl, cycloalkyl, $C_6$–$C_{12}$aryl, substituted alkyl, substituted cycloalkyl and substituted $C_6$–$C_{12}$aryl, and
$R^9$ and $R^{10}$ are independently selected from hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of alkoxy, acyloxy, aryloxy, —NR$^6$R$^6$, N-acylamino, oxo, hydroxy, —C(O)$OR^6$, —S(O)$_n$R$^6$, —C(O)NR$^6$R$^6$, —S(O)$_2$NR$^6$R$^6$, nitro, cyano, halogen, cycloalkyl, substituted cycloalkyl, $C_5$–$C_{12}$aryl, substituted $C_5$–$C_{12}$aryl and protected —OH where n and $R^6$ are as described above; or $R^9$ and $R^{10}$ taken together with the nitrogen to which they are attached represent a 5 to 6 member saturated ring containing up to one other heteroatom selected from oxygen and nitrogen;
m is 0–6; and
AR is selected from the group consisting of naphthalene, phenyl, pyrazole and phenanthrene; each of which is optionally substituted with one or more substituents selected from the group consisting of alkyl, cycloalkyl, substituted cycloalkyl, $C_5$–$C_{12}$aryl, substituted $C_5$–$C_{12}$aryl, aryloxy, hydroxy, alkoxy, acyloxy, —NR$^7$R$^8$, N-acylamino, N-sulfonylamino, nitro, cyano, halogen, —C(O)$OR^6$, —C(O)NR$^7$R$^8$, —S(O)$_2$NR$^7$R$^8$, —S(O)$_n$R$^6$, protected —OH, and alkyl substituted with one or more substituents selected from the group consisting of alkoxy, acyloxy, $C_5$–$C_{12}$aryl, substituted $C_5$–$C_{12}$aryl, —NR$^6$R$^6$, N-acylamino, oxo, hydroxy, cycloalkyl, substituted cycloalkyl, —C(O)$OR^6$, —C(O)NR$^7$R$^8$, —S(O)$_2$NR$^7$R$^8$, —S(O)$_n$R$^6$, aryloxy, nitro, cyano, halogen, and protected —OH; where
n is 0 to 3;
$R^6$ is selected from hydrogen, alkyl, cycloalkyl, $C_6$–$C_{12}$aryl, substituted alkyl, substituted cycloalkyl and substituted $C_6$–$C_{12}$aryl; and
$R^7$ and $R^8$ are independently hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of alkoxy, acyloxy, aryloxy, —NR$^6$R$^6$, N-acylamino, oxo, hydroxy, —C(O)$OR^6$, —S(O)$_n$R$^6$, —C(O)NR$^6$R$^6$, —S(O)$_2$NR$^6$R$^6$, nitro, cyano, cycloalkyl, substituted cycloalkyl, halogen, $C_6$–$C_{12}$aryl, substituted $C_6$–$C_{12}$aryl and protected —OH where n and $R^6$ are as described above; and
pharmaceutically acceptable salts, hydrates, solvates and esters thereof.

2. A method of claim 1 wherein the mammal is a human.

3. The method of claim 2 wherein the compound is selected from 3-hydroxy-4-[(2-hydroxy-1-naphthalenyl)azo-]-1-naphthalenesulfonic acid;
3-hydroxy-4-[(2-hydroxy-1-naphthalenyl)azo]-7-nitro-1-naphthalenesulfonic acid;
3-hydroxy-4-[(1-hydroxy-2-naphthalenyl)azo]-7-nitro-1-naphthalenesulfonic acid;
3-hydroxy-4-[(2-hydroxy-5-methyl-1-phenyl)azo]-1-naphthalenesulfonic acid;
3-hydroxy-4-[(1-hydroxy-2-naphthalenyl)azo]-1-naphthalenesulfonic acid;
3-hydroxy-4-[(5-hydroxy-3-methyl-1-phenyl-1H-pyrazol-4-yl)azo]-1-naphthalenesulfonic acid;
3-hydroxy-4-[(10-hydroxy-9-phenanthrenyl)azo]-1-naphthalenesulfonic acid;
3-hydroxy-4-[(2-hydroxy-7-methoxy-1-naphthalenyl)azo]-1-naphthalenesulfonic acid;
3-hydroxy-4-[(4-hydroxy-2-methoxy-1-naphthalenyl)azo]-1-naphthalenesulfonic acid;
4-[(1,3-dimethyl-5-hydroxy-1H-pyrazol-4-yl)azo]-3-hydroxy-1-naphthalenesulfonic acid;

3-hydroxy-4-{[5-hydroxy-1-(4-methylphenyl)-3-methyl-1H-pyrazol-4-yl]azo}-1-naphthalenesulfonic acid;
3-hydroxy-4-{[5-hydroxy-3-methyl-1phenyl-1H-pyrazol-4-yl)azo]-1-naphthalenecarboxylic acid;
3-hydroxy-4-{[5-hydroxy-3-methyl-1-(4-methylphenyl)-1H-pyrazol-4-yl]azo}-1-naphthalenecarboxylic acid;
4-{1-[3-(N-ethylsulfonamidophenyl)-5-hydroxy-3-methyl-1H-pyrazol-4-yl]azo}-3-hydroxy-1-naphthalenesulfonic acid;
4-[(3-ethoxycarbonyl-5-hydroxy-1-phenyl-1H-pyrazol-4-yl)azo]-3-hydroxy-1-naphthalenesulfonic acid;
3-hydroxy-4-{[5-hydroxy-3-methyl-1-(4-nitrophenyl)-1H-pyrazol-4-yl]azo}-1-naphthalenesulfonic acid;
4-{[3-tert-butyl-5-hydroxy-1-methyl-1H-pyrazol-4-yl]azo}-3-hydroxy-1-naphthalenesulfonic acid;
4-[(3-ethoxy-5-hydroxy-1-(4-nitrophenyl)-1H-pyrazol-4-yl)azo]-3-hydroxy-1-naphthalenesulfonic acid;
4-{[3-tert-butyl-5-hydroxy-1-phenyl-1H-pyrazol-4-yl]azo}-3-hydroxy-1-naphthalenesulfonic acid;
3-hydroxy-4-[(5-hydroxy-3-methyl-1-pyridin-2-yl-1H-pyrazol-4-yl)azo]-1-naphthalenesulfonic acid;
4-{[1-(4-benzyloxyphenyl)-5-hydroxy-3-methyl-1H-pyrazol-4-yl]azo}-3-hydroxy-1-naphthalenesulfonic acid;
3-hydroxy-4-{[5-hydroxy-3-methyl-1-(3-trifluoromethylphenyl)-1H-pyrazol-4-yl]azo}-1-naphthalenesulfonic acid;
4-{[1-(3,4-dimethylphenyl)-5-hydroxy-3-methyl-1H-pyrazol-4-yl]azo}-3-hydroxy-1-naphthalenesulfonic acid;
3-hydroxy-4-{[5-hydroxy-3-methyl-1-(3-nitrophenyl)-1H-pyrazol-4-yl]azo}-1-naphthalenesulfonic acid;
4-{[1-(4-fluorophenyl)-5-hydroxy-3-methyl-1H-pyrazol-4-yl]azo}-3-hydroxy-1-naphthalenesulfonic acid;
3-hydroxy-4-{[5-hydroxy-1-(4-iodophenyl)-3-methyl-1H-pyrazol-4-yl]azo}-1-naphthalenesulfonic acid;
3-hydroxy-4-{[5-hydroxy-3-methyl-1-(2-nitrophenyl)-1H-pyrazol-4-yl]azo}-1-naphthalenesulfonic acid;
4-{[1-(3,4-dimethylphenyl)-3-ethoxy-5-hydroxy-1H-pyrazol-4-yl]azo}-3-hydroxy-1-naphthalenesulfonic acid;
3-hydroxy-4-{[5-hydroxy-3-methyl-1-(4-trifluoromethylphenyl)-1H-pyrazol-4-yl]azo}-1-naphthalenesulfonic acid;
3-hydroxy-4-{[(5-hydroxy-3-methyl-1-(3-methylphenyl)-1H-pyrazol-4-yl]azo}-1-naphthalenesulfonic acid;
4-{[3-tert-butyl-1-(3,4-dimethylphenyl)-5-hydroxy-1H-pyrazol-4-yl]azo}-3-hydroxy-1-naphthalenesulfonic acid;
4-{[1-(3,4-dimethylphenyl)-5-hydroxy-3-phenyl-1H-pyrazol-4-yl]azo}-3-hydroxy-1-naphthalenesulfonic acid;
4-{[1-(3,4-Dimethylphenyl)-5-hydroxy-3-methyl-1H-pyrazol-4-yl]azo}-3-hydroxy-1-napthalenecarboxylic acid;
Methyl 5-{[1-(3,4dimethylphenyl)-5-hydroxy-3-methyl-1H-pyrazol-4-yl]azo}-6-hydroxy-2-napthalenecarboxylate;
1-{[1-(3,4-Dimethylphenyl)-5-hydroxy-3-methyl-1H-pyrazol-4-yl]azo}-2-hydroxynaphthalene;
3-Hydroxy-4-({5-hydroxy-1-[(4-methanesulfonyl)phenyl]-3-methyl-1H-pyrazol-4-yl}azo)-1-naphthalenesulfonic acid;
4-[(1-Benzyl-5-hydroxy-3-methyl-1H-pyrazol-4-yl)azo]-3-hydroxy-1-naphthalenesulfonic acid;
4-({1-[4-(Aminosulfonyl)phenyl]-5-hydroxy-3-methyl-1H-pyrazol-4-yl]azo)-3-hydroxy-1-naphthalenesulfonic acid; and
4-[(1-tert-Butyl-5-hydroxy-3-methyl-1H-pyrazol-4-yl)azo]-3-hydroxy-1-naphthalenesulfonic acid;

and pharmaceutically acceptable salts, hydrates, solvates and esters thereof.

4. The method of claim 3 wherein the compound is selected from
4-{[3-tert-butyl-1-(3,4-dimethylphenyl)-5-hydroxy-1H-pyrazol-4-yl]azo}-3-hydroxy-1-naphthalenesulfonic acid;
3-hydroxy-4-{[5-hydroxy-3-methyl-1-(3-trifluoromethylphenyl)-1H-pyrazol-4-yl]azo}-1-naphthalenesulfonic acid;
4-{[1-(3,4-dimethylphenyl)-5-hydroxy-3-methyl-1H-pyrazol-4-yl]azo}-3-hydroxy-1-naphthalenesulfonic acid;
3-hydroxy-4-{[5-hydroxy-1-(4-iodophenyl)-3-methyl-1H-pyrazol-4-yl]azo}-1-naphthalenesulfonic acid; and
4-{[1-(3,4-dimethylphenyl)-3-ethoxy-5-hydroxy-1H-pyrazol-4-yl]azo}-3-hydroxy-1-naphthalenesulfonic acid; and pharmaceutically acceptable salts, hydrates, solvates and esters thereof.

5. The method of claim 1 wherein the compound is administered orally.

6. The method of claim 1 wherein the compound is administered parenterally.

7. A method of enhancing platelet production in a mammal in need thereof which comprises administering to such mammal a therapeutically effective amount of a compound of Formula (II)

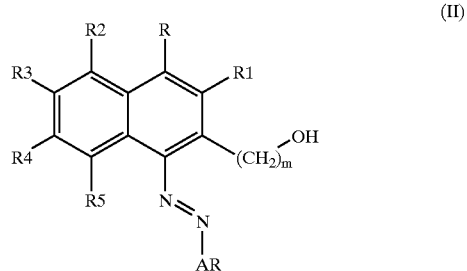

(II)

wherein:
R, $R^1$, $R^2$, $R^3$, $R^4$ and $R^5$ are each independently selected from hydrogen, —C(O)$OR^6$, —CON$R^9R^{10}$, —SO$_2$N$R^9R^{10}$, phosphonic acid, phosphinic acid, $C_{1-6}$alkyl, $C_{1-6}$alkoxy, —(CH$_2$)$_p$O$R^6$, nitro, cyano, halogen, —N$R^9R^{10}$, N-acylamino, N-sulfonylamino, —S(O)$_n$$R^6$, $C_5$–$C_{12}$aryl, substituted $C_5$–$C_{12}$aryl, alkyl, cycloalkyl, substituted cycloalkyl, protected —OH, and alkyl substituted with one or more substituents selected from the group consisting of alkoxy, acyloxy, $C_5$–$C_{12}$aryl, substituted $C_5$–$C_{12}$aryl, —N$R^9R^{10}$, N-acylamino, oxo, hydroxy, cycloalkyl, substituted cycloalkyl, —C(O)$OR^6$, —C(O)N$R^9R^{10}$, —S(O)$_2$N$R^9R^{10}$, —S(O)$_n$$R^6$, aryloxy, nitro, cyano, halogen, and protected —OH; where
n is 0 to 3;
p is 0–6;
$R^6$ is selected from hydrogen, alkyl, cycloalkyl, $C_6$–$C_{12}$aryl, substituted alkyl, substituted cycloalkyl and substituted $C_6$–$C_{12}$aryl, and
$R^9$ and $R^{10}$ are independently selected from hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of alkoxy, acyloxy, aryloxy, —N$R^6R^6$, N-acylamino, oxo, hydroxy, —C(O)$OR^6$, —S(O)$_n$$R^6$, —C(O)N$R^6R^6$, —S(O)$_2$N$R^6R^6$, nitro, cyano, halogen, cycloalkyl, substituted cycloalkyl, $C_5$–$C_{12}$aryl, substituted $C_5$–$C_{12}$aryl and protected —OH where n and $R^6$ are as described above; or $R^9$ and $R^{10}$ taken together with the nitrogen to which they are attached represent a 5 to 6 member saturated ring containing up to one other heteroatom selected from oxygen and nitrogen;

m is 0–6; and

AR is selected from the group consisting of naphthalene, phenyl, pyrazole and phenanthrene; each of which is optionally substituted with one or more substituents selected from the group consisting of alkyl, cycloalkyl, substituted cycloalkyl, $C_5$–$C_{12}$aryl, substituted $C_5$–$C_{12}$aryl, aryloxy, hydroxy, alkoxy, acyloxy, —$NR^7R^8$, N-acylamino, N-sulfonylamino, nitro, cyano, halogen, —C(O)$OR^6$, —C(O)$NR^7R^8$, —S(O)$_2$$NR^7R^8$, —S(O)$_n$$R^6$, protected —OH, and alkyl substituted with one or more substituents selected from the group consisting of alkoxy, acyloxy, $C_5$–$C_{12}$aryl, substituted $C_5$–$C_{12}$aryl, —$NR^6R^6$, N-acylamino, oxo, hydroxy, cycloalkyl, substituted cycloalkyl, —C(O)$OR^6$, —C(O)$NR^7R^8$, —S(O)$_2$$NR^7R^8$, —S(O)$_n$$R^6$, aryloxy, nitro, cyano, halogen, and protected —OH; where n is 0 to 3;

$R^6$ is selected from hydrogen, alkyl, cycloalkyl, $C_6$–$C_{12}$aryl, substituted alkyl, substituted cycloalkyl and substituted $C_6$–$C_{12}$aryl; and $R^7$ and $R^8$ are independently hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, —$NR^6R^6$, N-acylamino, oxo, hydroxy, —C(O)$OR^6$, —S(O)$_n$ $R^6$, —C(O)$NR^6R^6$, —S(O)$_2$$NR^6R^6$, nitro, cyano, cycloalkyl, substituted cycloalkyl, halogen, $C_6$–$C_{12}$aryl, substituted $C_6$–$C_{12}$aryl and protected —OH where n and $R^6$ are as described above; and pharmaceutically acceptable salts, hydrates, solvates and esters thereof.

8. A method of claim 7 wherein the mammal is a human.

9. The method of claim 8 wherein the compound is selected from 3-hydroxy-4-[(2-hydroxy-1-naphthalenyl)azo]-1-naphthalenesulfonic acid;

3-hydroxy-4-[(2-hydroxy-1-naphthalenyl)azo]-7-nitro-1-naphthalenesulfonic acid;

3-hydroxy-4-[(1-hydroxy-2-naphthalenyl)azo]-7-nitro-1-naphthalenesulfonic acid;

3-hydroxy-4-[(2-hydroxy-5-methyl-1-phenyl)azo]-1-naphthalenesulfonic acid;

3-hydroxy-4-[(1-hydroxy-2-naphthalenyl)azo]-1-naphthalenesulfonic acid;

3-hydroxy-4-[(5-hydroxy-3-methyl-1-phenyl-1H-pyrazol-4-yl)azo]-1-naphthalenesulfonic acid;

3-hydroxy-4-[(10-hydroxy-9-phenanthrenyl)azo]-1-naphthalenesulfonic acid;

3-hydroxy-4-[(2-hydroxy-7-methoxy-1-naphthalenyl)azo]-1-naphthalenesulfonic acid;

3-hydroxy-4-[(4-hydroxy-2-methoxy-1-naphthalenyl)azo]-1-naphthalenesulfonic acid;

4-[(1,3-dimethyl-5-hydroxy-1H-pyrazol-4-yl)azo]-3-hydroxy-1-naphthalenesulfonic acid;

3-hydroxy-4-{[5-hydroxy-1-(4-methylphenyl)-3-methyl-1H-pyrazol-4-yl]azo}-1-naphthalenesulfonic acid;

3-hydroxy-4-[(5-hydroxy-3-methyl-1-phenyl-1H-pyrazol-4-yl)azo]-1-naphthalenecarboxylic acid;

3-hydroxy-4-{[5-hydroxy-3-methyl-1-(methylphenyl)-1H-pyrazol-4-yl]azo}-1-naphthalenecarboxylic acid;

4-[1-[3-(N-ethylsulfonamidophenyl)-5-hydroxy-3-methyl-1H-pyrazol-4-yl]azo}-3-hydroxy-1-naphthalenesulfonic acid;

4-[(3-ethoxycarbonyl-5-hydroxy-1-phenyl-1H-pyrazol-4-yl)azo]-3-hydroxy-1-naphthalenesulfonic acid;

3-hydroxy-4-{[5-hydroxy-3-methyl-1-(4-nitrophenyl)-1H-pyrazol-4-yl]azo}-1-naphthalenesulfonic acid;

4-{[3-tert-butyl-5-hydroxy-1-methyl-1H-pyrazol-4-yl]azo}-3-hydroxy-1-naphthalenesulfonic acid 4-[(3-ethoxy-5-hydroxy-1-(4-nitrophenyl)-1H-pyrazol-4-yl)azo]-3-hydroxy-1-naphthalenesulfonic acid;

4-{[3-tert-butyl-5-hydroxy-1-phenyl-1H-pyrazol-4-yl]azo}-3-hydroxy-1-naphthalenesulfonic acid;

3-hydroxy-4-[(5-hydroxy-3-methyl-1-pyridin-2-yl-1H-pyrazol-4-yl)azo]-1-naphthalenesulfonic acid;

4-{[1-(4-benzyloxyphenyl)-5-hydroxy-3-methyl-1H-pyrazol-4-yl]azo}-3-hydroxy-1-naphthalenesulfonic acid;

3-hydroxy-4-{[5-hydroxy-3-methyl-1-(3-trifluoromethylphenyl)-1H-pyrazol-4-yl]azo}-1-naphthalenesulfonic acid;

4-{[1-(3,4-dimethylphenyl)-5-hydroxy-3-methyl-1H-pyrazol-4-yl]azo}-3-hydroxy-1-naphthalenesulfonic acid;

3-hydroxy-4-{[5-hydroxy-3-methyl-1-(3-nitrophenyl)-1H-pyrazol-4-yl]azo}-1-naphthalenesulfonic acid;

4-{[1-(4-fluorophenyl)-5-hydroxy-3-methyl-1H-pyrazol-4-yl]azo}-3-hydroxy-1-naphthalenesulfonic acid;

3-hydroxy-4-{[5-hydroxy-1-(4-iodophenyl)-3-methyl-1H-pyrazol-4-yl]azo}-1-naphthalenesulfonic acid;

3-hydroxy-4-{[5-hydroxy-3-methyl-1-(2-nitrophenyl)-1H-pyrazol-4-yl ]azo}-1-naphthalenesulfonic acid;

4-{[1-(3,4dimethylphenyl)-3-ethoxy-5-hydroxy-1H-pyrazol-4-yl]azo}-3-hydroxy-1-naphthalenesulfonic acid;

3-hydroxy-4-{[5-hydroxy-3-methyl-1-(4-trifluoromethylphenyl)-1H-pyrazol-4-yl]azo}-1-naphthalenesulfonic acid;

3-hydroxy-4-{[5-hydroxy-3-methyl-1-(3-methylphenyl)-1H-pyrazol-4-yl]azo}-1-naphthalenesulfonic acid;

4-{[3-tert-butyl-1-(3,4-dimethylphenyl)-5-hydroxy-1H-pyrazol-4-yl]azo}-3-hydroxy-1-naphthalenesulfonic acid;

4-{[1-(3,4-dimethylphenyl)-5-hydroxy-3-phenyl-1H-pyrazol-4-yl]azo}-3-hydroxy-1-naphthalenesulfonic acid;

4-{[1-(3,4-Dimethylphenyl)-5-hydroxy-3-methyl-1H-pyrazol-4-yl]azo}-3-hydroxy-1-napthalenecarboxylic acid;

Methyl 5-{[1-(3,4-dimethylphenyl)-5-hydroxy-3-methyl-1H-pyrazol-4-yl]azo}-6-hydroxy-2-napthalenecarboxylate;

1-{[1-(3,4-Dimethylphenyl)-5-hydroxy-3-methyl-1H-pyrazol-4-yl]azo}-2-hydroxynaphthalene;

3-Hydroxy-4-({5-hydroxy-1-[(4-methanesulfonyl)phenyl]-3-methyl-1H-pyrazol-4-yl}azo)-1-naphthalenesulfonic acid;

4-[(1-Benzyl-5-hydroxy-3-methyl-1H-pyrazol-4-yl)azo]-3-hydroxy-1-naphthalenesulfonic acid;

4-({1-[4-(Aminosulfonyl)phenyl]-5-hydroxy-3-methyl-1H-pyrazol-4-yl}azo)-3-hydroxy-1-naphthalenesulfonic acid; and 4-[(1-tert-Butyl-5-hydroxy-3-methyl-1H-pyrazol-4-yl)azo]-3-hydroxy-1-naphthalenesulfonic acid;

and pharmaceutically acceptable salts, hydrates, solvates and esters thereof.

10. A method of agonizing the TPO receptor in a mammal in need thereof which comprises administering an effective amount of a compound of Formula (II)

(II)

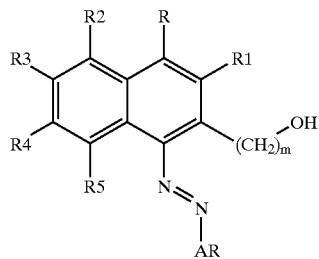

wherein:
R, R¹, R², R³, R⁴ and R⁵ are each independently selected from hydrogen, —C(O)OR⁶, —CONR⁹R¹⁰, —SO₂NR⁹R¹⁰, phosphonic acid, phosphinic acid, $C_{1-6}$alkyl, $C_{1-6}$alkoxy, —(CH₂)$_p$OR⁶, nitro, cyano, halogen, —NR⁹R¹⁰, N-acylamino, N-sulfonylamino, —S(O)$_n$R⁶, $C_5$–$C_{12}$aryl, substituted $C_5$–$C_{12}$aryl, alkyl, cycloalkyl, substituted cycloalkyl, protected —OH, and alkyl substituted with one or more substituents selected from the group consisting of alkoxy, acyloxy, $C_5$–$C_{12}$aryl, substituted $C_5$–$C_{12}$aryl, —NR⁹R¹⁰, N-acylamino, oxo, hydroxy, cycloalkyl, substituted cycloalkyl, —C(O)OR⁶, —C(O)NR⁹R¹⁰, —S(O)₂NR⁹R¹⁰, —S(O)$_n$R⁶, aryloxy, nitro, cyano, halogen, and protected —OH; where
n is 0 to 3;
p is 0–6;
R⁶ is selected from hydrogen, alkyl, cycloalkyl, $C_6$–$C_{12}$aryl, substituted alkyl, substituted cycloalkyl and substituted $C_6$–$C_{12}$aryl, and
R⁹ and R¹⁰ are independently selected from hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of alkoxy, acyloxy, aryloxy, —NR⁶R⁶, N-acylamino, oxo, hydroxy, —C(O)OR⁶, —S(O)$_n$ R⁶, —C(O)NR⁶R⁶, —S(O)₂NR⁶R⁶, nitro, cyano, halogen, cycloalkyl, substituted cycloalkyl, $C_5$–$C_{12}$aryl, substituted $C_5$–$C_{12}$aryl and protected —OH where n and R⁶ are as described above; or R⁹ and R¹⁰ taken together with the nitrogen to which they are attached represent a 5 to 6 member saturated ring containing up to one other heteroatom selected from oxygen and nitrogen;
m is 0–6; and
AR is selected from the group consisting of: naphthalene, phenyl, pyrazole and phenanthrene; each of which is optionally substituted with one or more substituents selected from the group consisting of alkyl, cycloalkyl, substituted cycloalkyl, $C_5$–$C_{12}$aryl, substituted $C_5$–$C_{12}$aryl, aryloxy, hydroxy, alkoxy, acyloxy, —NR⁷R⁸, N-acylamino, N-sulfonylamino, nitro, cyano, halogen, —C(O)OR⁶, —C(O)NR⁷R⁸, —S(O)₂NR⁷R⁸, —S(O)$_n$R⁶, protected —OH, and alkyl substituted with one or more substituents selected from the group consisting of: alkoxy, acyloxy, $C_5$–$C_{12}$aryl, substituted $C_5$–$C_{12}$aryl, —NR⁶R⁶, N-acylamino, oxo, hydroxy, cycloalkyl, substituted cycloalkyl, —C(O)OR⁶, —C(O)NR⁷R⁸, —S(O)₂NR⁷R⁸, —S(O)$_n$R⁶, aryloxy, nitro, cyano, halogen, and protected —OH; where
n is 0 to 3;
R⁶ is selected from hydrogen, alkyl, cycloalkyl, $C_6$–$C_{12}$aryl, substituted alkyl, substituted cycloalkyl and substituted $C_6$–$C_{12}$aryl; and R⁷ and R⁸ are independently hydrogen, cycloalkyl, $C_6$–$C_{12}$aryl, substituted cycloalkyl, substituted $C_6$14 $C_{12}$aryl, alkyl or alkyl substituted with one or more substituents selected from the group consisting of: alkoxy, acyloxy, aryloxy, —NR⁶R⁶, N-acylamino, oxo, hydroxy, —C(O)OR⁶, —S(O)$_n$R⁶, —C(O)NR⁶R⁶, —S(O)₂NR⁶R⁶, nitro, cyano, cycloalkyl, substituted cycloalkyl, halogen, $C_6$–$C_{12}$aryl, substituted $C_6$–C12aryl and protected —OH where n and R⁶ are as described above; and
pharmaceutically acceptable salts, hydrates, solvates and esters thereof.

11. A method of claim 10 wherein the mammal is a human.

12. A compound represented by the following Formula (I)

(I)

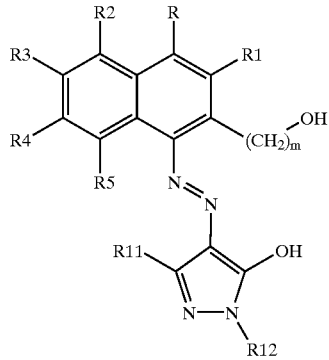

wherein:
R, R¹, R², R³, R⁴, R⁵ and R¹ are each independently selected from hydrogen, —C(O)OR⁶, —CONR⁹R¹⁰, phosphonic acid, phosphinic acid, $C_{1-6}$alkyl, $C_{1-6}$alkoxy, —(CH₂)$_p$OR⁶, nitro, cyano, halogen, —NR⁹R¹⁰, N-acylamino, N-sulfonylamino, —S(O)$_n$ R⁶, $C_5$–$C_{12}$aryl, substituted $C_5$–$C_{12}$aryl, alkyl, cycloalkyl, substituted cycloalkyl, protected —OH, and alkyl substituted with one or more substituents selected from the group consisting of alkoxy, acyloxy, $C_5$–$C_{12}$aryl, substituted $C_5$–$C_{12}$aryl, —NR⁹R¹⁰, N-acylamino, oxo, hydroxy, cycloalkyl, substituted cycloalkyl, —C(O)OR⁶, —C(O)NR⁹R¹⁰, —S(O)₂NR⁹R¹⁰, —S(O)$_n$R⁶, aryloxy, nitro, cyano, halogen, and protected —OH; where
n is 0–3;
p is 0–6;
R⁶ is selected from hydrogen, alkyl, cycloalkyl, $C_6$–$C_{12}$aryl, substituted alkyl, substituted cycloalkyl and substituted $C_6$–$C_{12}$aryl; and
R⁹ and R¹⁰ are independently selected from hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of alkoxy, acyloxy, aryloxy, —NR⁶R⁶, N-acylamino, oxo, hydroxy, —C(O)OR⁶, —S(O)$_n$ R⁶, —C(O)NR⁶R⁶, —S(O)₂NR⁶R⁶, nitro, cyano, cycloalkyl, substituted cycloalkyl, $C_5$–$C_{12}$aryl, substituted $C_5$–$C_{12}$aryl and protected —OH where n and R⁶ are as described above; or R⁹ and R¹⁰ taken together with the nitrogen to which they are attached represent a 5 to 6 member saturated ring containing up to one other heteroatom selected: from oxygen and nitrogen;
m is 0–6; and R¹² is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, cycloalkyl, substituted cycloalkyl, $C_5$–$C_{12}$aryl, substituted $C_5$–$C_{12}$aryl, aryloxy, alkoxy, acyloxy, amino, nitro, cyano, halogen, hydroxy, protected —OH, and alkyl substituted with one or more substituents selected from the group consisting of: alkoxy, acyloxy, $C_5$–$C_{12}$aryl, substituted $C_5$–$C_{12}$aryl, cycloalkyl, substituted cycloalkyl, aryloxy, amino, nitro, cyano, halogen, hydroxy, and protected —OH; and pharmaceutically acceptable salts, hydrates, solvates and esters thereof;

provided that:

at least one of R, $R^1$, $R^2$, $R^3$, $R^4$, $R^5$ or $R^{11}$ is selected from: sulfonic acid, —C(O)OR⁶, —CONR⁹R¹⁰, phosphonic acid and phosphinic acid; where $R^6$, $R^9$ and $R^{10}$ are as described above; and provided that:

when R is sulfonic acid, $R^{12}$ does not equal unsubstituted phenyl or 4-methylphenyl.

13. A compound of claim 12 selected from 3-hydroxy-4-[(5-hydroxy-3-methyl-1-phenyl-1H-pyrazol-4-yl)azo]-1-naphthalenecarboxylic acid;
3-hydroxy-4-{[5-hydroxy-3-methyl-1-(4-methylphenyl)-1H-pyrazol-4-yl]azo}-1-naphthalenecarboxylic acid;
3-hydroxy-4-{[5-hydroxy-3-methyl-1-(4-nitrophenyl)-1H-pyrazol-4-yl]azo}-1-naphthalenesulfonic acid;
4-{[3-tert-butyl-5-hydroxy-1-methyl-1H-pyrazol-4-yl]azo}-3-hydroxy-1-naphthalenesulfonic acid;
4-{[3-tert-butyl-5-hydroxy-1-phenyl-1H-pyrazol-4-yl]azo}-3-hydroxy-1-naphthalenesulfonic acid;
3-hydroxy-4-[(5-hydroxy-3-methyl-1-pyridin-2-yl-1H-pyrazol-4-yl)azo]-1-naphthalenesulfonic acid;
4-{[1-(4-benzyloxyphenyl)-5-hydroxy-3-methyl-1H-pyrazol-4-yl]azo}-3-hydroxy-1-naphthalenesulfonic acid;
3-hydroxy-4-{[5-hydroxy-3-methyl-1-(3-trifluoromethylphenyl)-1H-pyrazol-4-yl]azo}-1-naphthalenesulfonic acid;
4-{[1-(3,4-dimethylphenyl)-5-hydroxy-3-methyl-1H-pyrazol-4-yl]azo}-3-hydroxy-1-naphthalenesulfonic acid;
3-hydroxy-4-{[5-hydroxy-3-methyl-1-(3-nitrophenyl)-1H-pyrazol-4-yl]azo}-1-naphthalenesulfonic acid;
4-{[1-(4-fluorophenyl)-5-hydroxy-3-methyl-1pyrazol-4-yl]azo}-3-hydroxy-1-naphthalenesulfonic acid;
3-hydroxy-4-{[5-hydroxy-1-(4-iodophenyl)-3-methyl-1H-pyrazol-4-yl]azo}-1-naphthalenesulfonic acid;
3-hydroxy-4-{[5-hydroxy-3-methyl-1-(2-nitrophenyl)-1H-pyrazol-4-yl]azo}-1-napthalenesulfonic acid;
4-{[1-(3,4-dimethylphenyl)-3-ethoxy-5-hydroxy-1H-pyrazol-4-yl]azo}-3-hydroxy-1-naphthalenesulfonic acid;
3-hydroxy-4-{[5-hydroxy-3-methyl-1-(4-trifluoromethylphenyl)-1H-pyrazol-4-yl]azo}-1-naphthalenesulfonic acid;
3-hydroxy-4-{[5-hydroxy-3-methyl-1-(3-methylphenyl)-1H-pyrazol-4-yl]azo}-1-naphthalenesulfonic acid;
4-{[3-tert-butyl-1-(3,4-dimethylphenyl)-5-hydroxy-1H-pyrazol-4-yl]azo}-3-hydroxy-1-naphthalenesulfonic acid;
4-{[1-(3,4-dimethylphenyl)-5-hydroxy-3-phenyl-1H-pyrazol-4-yl]azo}-3-hydroxy-1-naphthalenesulfonic acid;
4-{[1-(3,4-Dimethylphenyl)-5-hydroxy-3-methyl-1H-pyrazol-4-yl]azo}-3-hydroxy-1-napthalenecarboxylic acid;
Methyl 5-{[1-(3,4-dimethylphenyl)-5-hydroxy-3-methyl-1H-pyrazol-4-yl]azo}-6-hydroxy-2-napthalenecarboxylate;
1-{[1-(3,4-Dimethylphenyl)-5-hydroxy-3-methyl-1H-pyrazol-4-yl]azo}-2-hydroxynaphthalene; and
4-[(1-Benzyl-5-hydroxy-3-methyl-1H-pyrazol-4-yl)azo]-3-hydroxy-1-naphthalenesulfonic acid; and pharmaceutically acceptable salts, hydrates, solvates and esters thereof.

14. A compound of claim 13 selected from

4-{[3-tert-butyl-1-(3,4-dimethylphenyl)-5-hydroxy-1H-pyrazol-4-yl]azo}-3-hydroxy-1-naphthalenesulfonic acid;
3-hydroxy-4-{[5-hydroxy-3-methyl-1-(3-trifluoromethylphenyl)-1H-pyrazol-4-yl]azo}-1-naphthalenesulfonic acid;
4-{[1-(3,4-dimethylphenyl)-5-hydroxy-3-methyl-1H-pyrazol-4-yl]azo}-3-hydroxy-1-naphthalenesulfonic acid;
3-hydroxy-4-{[5-hydroxy-1-(4-iodophenyl)-3-methyl-1H-pyrazol-4-yl]azo}-1-napthalenesulfonic acid; and
4-{[1-(3,4-dimethylphenyl)-3-ethoxy-5-hydroxy-1H-pyrazol-4-yl]azo}-3-hydroxy-1-naphthalenesulfonic acid; and pharmaceutically acceptable salts, hydrates, solvates and esters thereof.

15. A pharmaceutical composition comprising a therapeutically effective amount of a compound according to claim 12 and at least one pharmaceutically acceptable carrier or diluent.

* * * * *